United States Patent
Rodríguez Zapata et al.

(10) Patent No.: US 11,292,818 B2
(45) Date of Patent: Apr. 5, 2022

(54) ISOLATED TRANSCRIPTION FACTORS OF CARICA PAPAYA AND THEIR APPLICATION TO OBTAIN EXTREME TEMPERATURE TOLERATING PLANTS

(71) Applicant: CENTRO DE INVESTIGACIÓN CIENTÍFICA DE YUCATÁN, A.C., Yucatán (MX)

(72) Inventors: Luis Carlos Rodríguez Zapata, Mérida (MX); Luis Joel Figueroa Yañez, Mérida (MX); Alejandro Pereira Santana, Mérida (MX); Enrique Castaño De La Serna, Mérida (MX)

(73) Assignee: ENTRO DE INVESTIGACIÓN CIENTÍFICA DE YUCATÁN, A.C., Yucatán (MX)

( * ) Notice: Subject to any disclaimer, the term of this patent is extended or adjusted under 35 U.S.C. 154(b) by 0 days.

(21) Appl. No.: 16/316,195

(22) PCT Filed: Jun. 30, 2017

(86) PCT No.: PCT/MX2017/000071
§ 371 (c)(1),
(2) Date: Jan. 8, 2019

(87) PCT Pub. No.: WO2018/009050
PCT Pub. Date: Jan. 11, 2018

(65) Prior Publication Data
US 2021/0087235 A1 Mar. 25, 2021

(30) Foreign Application Priority Data
Jul. 8, 2016 (MX) .................. MX/A/2016/008991

(51) Int. Cl.
*C07K 14/415* (2006.01)
*C12N 15/82* (2006.01)

(52) U.S. Cl.
CPC ........ *C07K 14/415* (2013.01); *C12N 15/8273* (2013.01)

(58) Field of Classification Search
None
See application file for complete search history.

(56) References Cited

U.S. PATENT DOCUMENTS

| | | |
|---|---|---|
| 7,479,584 B2 | 1/2009 | Tomes et al. |
| 7,807,869 B1 | 10/2010 | Schnabel et al. |
| 2004/0078852 A1 | 4/2004 | Thomashow et al. |
| 2008/0016593 A1 | 1/2008 | Gal-On et al. |
| 2008/0172765 A1 | 7/2008 | Katagiri et al. |
| 2008/0271211 A1 | 10/2008 | Polston et al. |
| 2009/0265813 A1 | 10/2009 | Gutterson et al. |
| 2010/0115665 A1 | 5/2010 | Czosnek |
| 2015/0067916 A1 | 3/2015 | Arce Johnson et al. |

FOREIGN PATENT DOCUMENTS

| | | |
|---|---|---|
| WO | 1999041974 A1 | 8/1999 |
| WO | 2006007557 A2 | 1/2006 |
| WO | 2006033708 A1 | 3/2006 |
| WO | 2012140230 A1 | 10/2012 |
| WO | 2014160304 A1 | 10/2014 |

OTHER PUBLICATIONS

Zhang (2003) Curr Opin Plant Biol 6:430-40.*
Olsen et al. (2005) Trends Plant Sci 10(2):79-87.*
Guo et al. (2004) Proc Natl Acad Sci USA 101:9205-10.*
Thieme et al. (2015) Nat Plants 1:15025.*
Ming et al. (2008) Nature 452:991-96.*
Arroyo-Herrera Ana et al.; A novel Dreb2-type gene from Carica papaya confers tolerance under abiotic stress; Plant Cell Tissue and Organ Culture Apr. 2016. vol. 125, NT' 1, pp. 119-133.
Li Xueptng et al.; Isolation and characterization of ethylene response factor family genes during development, ethylene regulation and stress treatments in papaya fruit; Plant Physiology and Biochemistry; (Paris) Sep. 2013; vol. 70, pp. 81-92.
Lin Rong-Cheng et al.; Role of Arabidopsis RAP2.4 in Regulating Light- and Ethylene-Mediated Developmental Processes and Drought Stress Tolerance; Molecular Plant Jan. 2008; vol. 1; N° 1; pp. 42-57.
Jisha, V. et al.. Overexpression of an AP2/ERF Type Transcription Factor OsEREBPI Confers Biotic and Abiotic Stress Tolerance in Rice; PLoS One, Jun. 2015, vol. 10, N° 6, pp. 1-24.
Mizoi Junya et al.; AP2/ERF family transcription factors in plant abiotic stress responses; Biochimica et Biophysica Acta; Gene Regulatory Mechanisms Feb. 2012; vol. 1819, N° 2, Sp. Iss. SI, pp. 86-96.
Figueroa-Yanez Luis et al.; RAP2.4a Is Transported through the Phloem to Regulate Cold and Heat Tolerance in Papaya Tree (Carica papaya cv. Maradol): Implications for Protection Against Abiotic Stress; PLoS One; Oct. 20, 2016; vol. 11, N° 10; pp. 1-24.

(Continued)

*Primary Examiner* — Russell T Boggs
(74) *Attorney, Agent, or Firm* — Shumaker, Loop & Kendrick, LLP

(57) ABSTRACT

The hereby invention provides four genes CpRap2 isolated from *Carica papaya* identified as CpRap2.4a, CpRap2.4b, CpRap2.1, CpRap2.10 and that consist of SEQ. ID NO: 1, SEQ. ID NO: 2, SEQ. ID NO: 3 and SEQ. ID NO: 4, as well as the genetic transformation methods for the overexpression of these genes and the obtaining of tolerant non-transgenic plants through grafts. Genetic transformation of plants that overexpress genes CpRap2 and their grafts showed they could survive extreme temperatures up to 12 days for heat and more than 30 days for cold.

5 Claims, 9 Drawing Sheets

Specification includes a Sequence Listing.

(56) References Cited

OTHER PUBLICATIONS

International Search Report dated Dec. 20, 2017 in International Patent Application No. PCT/MX2017/000071.
Written Opinion dated Dec. 20, 2017 in International Patent Application No. PCT/MX2017/000071.

* cited by examiner

FIG. 1

ISOLATED TRANSCRIPTION FACTORS OF CARICA PAPAYA AND THEIR APPLICATION TO OBTAIN EXTREME TEMPERATURE TOLERATING PLANTS

REFERENCE TO AN ELECTRONIC SEQUENCE LISTING

The contents of the electronic sequence listing (5309_18US-A_ST25.txt; Size: 16 KB; and Date of Creation: Mar. 30, 2021) is herein incorporated by reference in its entirety.

FIELD OF THE INVENTION

The hereby invention belongs to the biotechnology field, specifically to the genetic engineering field and molecular biology of plants with potential application in agriculture and describes the use of transcription factors of the RAP 2 family isolated from the *Carica papaya* as well as their application, under different techniques, particularly using the Graft technique to create plants that are stress tolerant due to extreme temperatures.

BACKGROUND OF THE INVENTION

The papaya (*Carica papaya* L.) is the fruit of most economic importance belonging to the Caricaceae family, the biggest production areas are found in the tropical and subtropical countries with an estimate world production of 12.4 million tons until 2012 (FAO. (2015). Food and Agricultural Organization). The papaya is known for its nutritional benefits and medicinal applications (Gurudata M., Deshmukh Y. A. and Naikwadi A. A. (2015). Anticancer effects of *Carica papaya* in experimental induced mammary tumors in rats. *International Journal of Medical Research & Health Sciences* 4(1):667-671). It is also known, that its productivity is significantly reduced when it is affected by several types of stress, such as drought, extreme temperatures and salinity, etc. (Campostrini E. and Glenn D. M. (2007). Ecophysiology of papaya: a review. *Braz. J. Physiol.*, 19(4):413-424). Therefore, in the future it will be needed to improve the tolerance of the papaya crops to abiotic stress.

Likewise, agriculture faces challenges related to the variability of temperatures linked to climate changes. It is well known that the crop yield is brought down either by elevated as well as by low temperatures. To face this situation, diverse strategies that go from the handling of parcels or greenhouses to choosing varieties suitable for extreme weather are used, but which are not the most attractive, commercially speaking.

One of the options that has currently been used to solve this type of problem is genetic transformation of plants, by means of insertion of genes that can confer them tolerance or resistance to diverse biotic and abiotic factors. It is well known that the tolerance of plants to these types of stress depends on the regulation of cascades of biochemical and molecular networks involved in the perception of stress, signal transduction and the expression of specific genes related to certain environmental limit. The key components that control and modulate the acclimatization to stress are the transcription factors which are small proteins that regulate the expression of many other genes that originate the modulation of complex acclimatization mechanisms so that they form an interesting group of molecules to be used in the transformation of plants so that they become tolerant to diverse factors. Hence this invention is focused on the use of transcription factors for conferring resistance to extreme temperatures.

Transcription factors (TSF) are proteins that modulate the transcriptional activity, that is, they propitiate the access of the RNA polymerases to the DNA mold strand that will be transcribed (Udvardi M., Kakar K., Wandrey M., Montanari O., Murray J., Andriankaja A., Zhang J. Y., Benedito V., Hofer J. M. I., Chueng F., and Town C. D. (2007). Legume Transcription factors: Global regulators of plant development and response to the environment. *Plant Physiology*, 144(2):538-549). Some of these TSF are involved in the tolerance to abiotic stress and belong to the super family APETALA2/response Element to Ethylene (AP2/ERF) which feature is that it has the AP2/ERF domain that approximately consists of 60 to 70 amino acids and is involved in the link with the DNA. This super family is composed of three: a) proteins of the AP2 family, which include two repeated domains AP2/ERF, b) proteins of the ERF family, that include an only domain AP2/ERF and finally c) proteins of the RAV family, which include a B3 domain and an only AP2/ERF domain (Riechmann J L, Heard J, Martin G, Reuber L, Jiang C, Keddie J, Adam L, Pineda O, Ratcliffe O J, Samaha R R, et al., (2000). *Arabidopsis* transcription factors: genome-wide comparative analysis among eukaryotes. *Science* 290: 2105-2110; Sakuma Y, Liu Q, Dubouzet J G, Abe H, Shinozaki K, Yamaguchi-Shinozaki K (2002) DNA-binding specificity of the ERF/AP2 domain of *Arabidopsis* DREBs, transcription factors involved in dehydration- and cold-inducible gene expression. *Biochem Biophys Res Commun* 290:998-1009 and Nakano T, Suzuki K, Fujimura T, and Shinshi H. (2006). Genome-wide analysis of the ERF gene family in *Arabidopsis* and Rice. *Plant Physiol.* 140:411-432).

The ERF family is divided into two sub families, the first one, called the ERF sub family and the second called CBF/response element to dehydration (DREB), in which the RAP genes that are related to the current invention are related (Sakuma Y, Liu Q, Dubouzet J G, Abe H, Shinozaki K, Yamaguchi-Shinozaki K (2002) DNA-binding specificity of the ERF/AP2 domain of *Arabidopsis* DREBs, transcription factors involved in dehydration- and cold-inducible gene expression. *Biochem Biophys Res Commun* 290:998-1009). However, on Nakano T, Suzuki K, Fujimura T, and Shinshi H. (2006). Genome-wide analysis of the ERF gene family in *Arabidopsis* and Rice. *Plant Physiol.* 140:411-432 published that on *Arabidopsis thaliana* there are 122 transcription factors that belong to the ERF family, which were re-classified in twelve groups that go from I to X plus besides VI-L and Xb-L. Through bioinformatic analyses performed during that work and based on the preservation the RAP transcription factors were reorganized among different new groups, so they are as follows a) RAP2.4 inside group I; b) RAP2.1, RAP2.9 and RAP2.10 on group II; c) RAP2.11 on group V; d) RAP2.2, RAP2.3 and RAP2.12 on group VII; e) RAP2.5 n group VIII and f) RAP2, on group X. It is worth mentioning that all RAP2 sequences have an only AP2 domain that is quite preserved. However, in the distinct groups in which they are classified, the structure of their motifs varies.

Among group I, some variants called RAP2.4A and RAP2.4B have been found within the state of the art. For example, Lin R C, Park H J, Wang H Y. Role of *Arabidopsis* RAP2.4 in regulating light- and ethylene-mediated developmental processes and drought stress tolerance. *Mol Plant*. 2008; 1: 42-57.characterized the RAP2.4 and RAP2.4A genes, in *Arabidopsis thaliana*, proposing that RAP2.4 acts as a downstream transcriptional activator and that this activation converges at any point in the light and ethylene signaling paths to regulate coordinately multiple processes of development and response to stress. On the other hand, in 2011, Rae L, Lao N T, Kavanagh T A. Regulation of multiple aquaporin genes in *Arabidopsis* by a pair of recently duplicated DREB transcription factors. *Planta*. 2011; 234: 429-444 observed that RAP2.4B and RAP2.4 transcription factors on *Arabidopsis thaliana* give as initial response the positive regulation of the expression of aquaporin genes from a stress caused by water deficit. On the same research, it was also proven that, once the plants are dehydrated by exposure to low temperatures and osmotic stress, these present a similar pattern in the accumulation of transcripts, probably due to crosstalk. Finally, these authors concluded that RAP2.4B is stress inducible by heat and that RAP2.4 is not sensitive to this type of stress.

In the state of the art there have been some patents identified which use RAP2 transcription factors that intend to generate plants with a better response to different stress types. Some of them are described as follows.

Our work team developed the patent application with publication number MX/a/2015/017242 in which it was overexpressed the CpDREB2 transcription factor that also belongs to the AP2/ERF super family; overexpression of CpDREB2 confers tolerance to elevated temperatures for 6 days and to low temperatures for 35 days. It is worth mentioning that even when tolerance to elevated and low temperatures is like the characteristics that are stated in this invention, only transgenic plants that overexpress such gen can acquire tolerance to abiotic stress and this tolerance cannot be transferred to grafts as it is further described in this invention.

Concerning other reported patents with transcription factors like those stated in this invention we can mention the US patent application US 20040078852 A1 that reports two transcription factors ZAT12 and Rap2.1 in *Arabidopsis thaliana*, that are regulated by short term cold, expressing the ZAT12 gen up to 24 hours and the Rap2.1 gen is only expressed by (7) seven days.

On the other hand, in the US patent application US 20090265813 A1, reference is made to the overexpression of different transcription factors type RAP2 in plants with the purpose of obtaining transgenic overexpressing plants more resistant to diseases (in some cases to more than one pathogen) or more tolerant to an abiotic stress (hypoxia, salinity, heat, cold, drought or little nitrogenation). It was observed that the plants that overexpressed the construct G9 with the Rap2.8 and RAV components increased their tolerance to salinity and to cold. However, this patent does not show a real test of the tolerance to such stress, since they only show transcriptomic analyses and not tests with tolerant plants.

In the International patent application WO 2006007557 A2 genes and proteins are related, and methods that include or use the C-repeated union factors (CBF), specifically CBF3 on Rye grass Zacate, additionally showing, that the overexpression of the APS-2 (RAP2.11) transcription factor and others can generate plants with a better response to drought, salinity and low temperatures. In the International patent application WO 2014160304 A1 there are improvements proposed for the adaptation of corn referring to a method for creating corn plants that adapt to certain geographic conditions and that express certain characteristics of agronomical importance referring to the overexpression of Rap2.7 gen to modulate the floral transition of the corn. It is worth mentioning that the two aforementioned patents refer to genes that could only work in vegetable models of monocotyledons such as the Rye grass zacate and corn. Unlike the genes that are explained in the hereby invention and that proceed from *Carica papaya* var. Maradol that is a dicotyledonous culture and that these gens can be implemented in all the existing dicotyledonous models of commercial importance.

In the international patent application WO 1999041974 A1 it is described the use of the Rap2.1, Rap2.2, Rap2.3, Rap2.4, Rap2.5, Rap2.6, Rap2.7, Rap2.8 and Rap2.9 genes to obtain a method that modulates cell mass in seeds and in other parts of soy and canola plants. Also, the U.S. Pat. No. 7,479,584 B2 describes the Rap2.7 isolated corn gen whose potential is to accelerate or to delay flowering of plants. On these patents, they do not specify in any point their use to confer tolerance to abiotic stress.

As it can be seen many transcription factors type RAP2 respond to abiotic stress according to the publication journals and patents. However, the overexpression of neither of them confers the plants with elevated or low temperature tolerance for long time such as happens with the genes that are described in the hereby invention. Towards this concern the invention provides these sequences that are useful to generate transgenic plants tolerant to elevated and low temperatures, being particularly useful SEQ ID NO: 1, SEQ ID NO: 2 and SEQ ID NO: 4 for those plants which are exposed to elevated temperatures, and SEQ ID NO: 1, SEQ ID NO: 2, SEQ ID NO: 3 and SEQ ID NO: 4 are particularly useful for those plants exposed to low temperatures. Additionally, these transgenic plants can serve as rootstocks to confer tolerance to elevated and low temperatures to their non-transgenic grafts. An additional value to the hereby invention is that these plants, the transgenic and their grafts, can withstand better extreme temperatures and for a longer amount of time if they are repeatedly exposed to sudden temperature changes.

Even more, in the case of amino acid sequences that have to do with the hereby invention, identified as SEQ ID NO: 5, SEQ ID NO: 6, SEQ ID NO: 7 and SEQ ID NO: 8 (see listing of sequences), it was further observed that the motifs CMI-1, CMI-2, CMI-3 and CMI-4 are not identical with each other, and neither with respect to the *Arabidopsis thaliana* ones. Therefore, it is established that the CpRap2.4a, CpRap2.4b, CpRap2.1 and CpRap2.10 genes, corresponding to the aforementioned sequences object of the hereby invention are orthologous genes of *Arabidopsis thaliana*, whose functions do not follow the responses to stress expressed in other species of plants including the *Arabidopsis thaliana*.

Additionally, the hereby invention provides a technique that allows the type RAP2 transcription factors that codify for proteins: CpRAP2.4a, CpRAP2.4b, CpRAP2.1 and CpRAP2.10, respond to abiotic stress caused by extreme temperatures in transgenic plants and their grafts. Thus, it is proven that there is a dynamic signage in the response to abiotic stress through the whole plant which is besides transmissible to grafts. The above shall allow to generate grafts whose products such as flowers and fruits are not transgenic, in which the sequences related with genetic transformation (vectors, resistance genes, etc.) would not be detected, opening doors to new markets such as the European one.

On the other hand, this invention allows solving a problem for the culture of plants that are susceptible to extreme temperatures. Currently the existing alternatives in the market to mitigate this effect are: building greenhouses with controlled humidity and temperatures, implementing an irrigation infrastructure for large tracts of land; however, it is needed a big economic investment and on the other hand the generated transgenic plants have acceptance limitation on certain markets where there is no place for transgenic products.

That is why through the current invention provides an alternative to obtain plants that are tolerant to certain types of stress by means of grafts bound to a transgenic plant. The long-distance communication or flow of genes and transcripts that respond to certain types of stress has been already described in the state of the art such as diverse patent documents show. Such is the case of the US patent US2008016593 A1 where there is used a transformed pattern which resists to viral diseases attached to a susceptible graft and the resistance to disease is conferred to the graft by means of the link with the viral disease resisting rootstock. The invention refers to the methods to produce viral resistance grafted plants. Likewise, US patent applications US 20080271211 A1, US 20100115665 A1, US2015067916 A1 and patent U.S. Pat. No. 7,807,869 B1 use a transgenic rootstock or one transformed from a plant to confer resistance to pathogens to a determine done with the limitation that it is not mentioned the resistance or tolerance to abiotic stress such as extreme temperatures.

In the international patent application WO 2012140230 A1 it is described the generation of different non-transgenic plants with modified phenotypes by means of the transmission of a transcriptional gene regulation signal RNA from the rootstock to the graft. The invention mentions altered rootstocks by means of RNA mediated transcriptional regulation besides inducing gene silencing and cisgenic regulation to modify the phenotype of the grafted plants. However, there are no concrete evidence of the experiments that backup these statements. The hereby invention has the advantage with respect to the latter that it shows that on the experiments of tolerance to heat and cold transgenic plants can tolerate these conditions for long times and when creating a graft this can acquire such characteristics, without resulting on a transgenic product.

In some studies, it has been mentioned that the AP2 type transcription factors are exclusively located at the nucleus of cells (Shigyo M. and I to M. (2004). Analysis of gymnosperm two-AP2-domain-containing genes. *Development genes and Evolution*, 214:105-114), even though some like Bai X., Rivera-Vega L., Mamidala P., Bonello P., Herms D. A. and Mittapalli O. (2011). Transcriptomic signatures of ash (*Fraxinus* spp.) phloem. *PLoS One*. 6:e16368, suggest that some messenger RNAs belonging to the AP2 superfamily are found in the sap, as described for the *Fraxinus* spp plant, however it does not refer to the possible transfer of RNAs through grafts, much less provides evidence that they confer resistance or tolerance to extreme temperatures. Towards this concern the hereby invention proves the presence of type Rap2 messenger RNAs in the sap of the *Carica papaya* var. Maradol and proposes the use of grafts for the generation of plants tolerant to extreme temperatures by using the sequences described in the hereby invention thus providing non-transgenic plants that present that tolerance. Besides it is worth mentioning that not all Rap2 messenger RNAs can travel through the phloem, either the ability to confer tolerance to the abiotic stress that are declared in the hereby invention, since to determine the functionality and the abilities of all the Rap2 genes it would be needed years of exhaustive research.

This is how the hereby invention provides isolated genes from *Carica papaya* var. Maradol, called CpRap2.4a, CpRap2.4b, CpRap2.1 and CpRap2.10 that consist of the nucleotide sequences ordered in SEQ ID NO: 1, SEQ ID NO: 2, SEQ ID NO: 3 and SEQ ID NO: 4, besides it describes a genetic transformation method for the overexpression of genes and the utilization of the graft technique to transfer tolerance or resistance to extreme temperatures during long times (from a rootstock to a scion) to give as a result grafts with tolerance to stress qualities in response to exposure to extreme temperatures. Tobacco plants (transgenic lines and grafts) that overexpress the Rap2 genes, have the ability to survive to extreme temperatures during long periods of time in relation to the control plants (not transgenic) These transgenic plants evidently respond to stress differentially and either messenger RNAs as proteins move from one side to the other in the graft, which is not mentioned in any of the patents described in the state of the art, conferring them a clear advantage to achieve an innovation product of great potential to be traded in markets with restricted access to transgenic products.

SUMMARY OF THE INVENTION

As a first embodiment of the invention an alternative for the generation of plants tolerant to extreme temperatures, is provided.

Another embodiment of the hereby invention is to provide isolated sequences of *C. papaya* var. Maradol that allow the generation of plants tolerant to extreme temperatures.

An additional embodiment of the hereby invention is to provide functional nucleotide sequences of transcription factors called CpRap2.4a, CpRap2.4b, CpRap2.1 and CpRap2.10 isolated genes of *Carica papaya* var. Maradol that confer tolerance to extreme temperatures in plants.

Another embodiment of the hereby intervention is to provide amino acid sequences that are part of the proteins that result from the overexpression of transcription factors called CpRap2.4a, CpRap2.4b, CpRap2.1 and CpRap2.10 isolated genes of *Carica papaya* Maradol var. that confer tolerance to extreme temperatures in plants.

Another embodiment of the hereby invention is to provide pairs of specific primers for the cloning of CpRap2.4a, CpRap2.4b, CpRap2.1 and CpRap2.10 genes in binary vectors.

Another embodiment of the hereby invention is to provide pairs of specific primers for the amplification, isolation and identification of CpRap2.4a, CpRap2.4b, CpRap2.1 and CpRap2.10 genes.

Another embodiment of the hereby invention is to provide transcription factors that can be transferred to grafts, to improve the tolerance to extreme temperatures in plants.

Another embodiment of the hereby invention is to provide transcription factors that allow the generation of transgenic plants tolerant or resistant to abiotic stress due to extreme temperatures.

An additional embodiment of the hereby invention is to provide resistant or tolerant plants to abiotic stress due to extreme temperatures obtained through grafts.

Another embodiment of the hereby invention is to provide the methodology to generate transgenic plants tolerant or resistant to abiotic stress due to extreme temperatures.

Finally, another embodiment of the hereby invention is to provide a methodology for the generation of grafts which are tolerant or resistant to abiotic stress due to extreme temperatures.

BRIEF DESCRIPTION OF THE FIGURES

FIG. 1 shows a diagram with multiple alignments of predicted amino acid sequences of the RAP2.4a, RAP2.4b (group I) proteins, where the domain AP2/ERF of *C. papaya* var. Maradol compared to RAP proteins of different related species can be seen. The protein sequences were aligned using ClustalW2 and the identity or similarity of amino acids is shown on BOXSHADE format. For RAP2.4 sequences the AP2/ERF domain (○ shows the beginning and the end of the AP2/ERF domain) and the CMI-1motifs (✚ show the beginning and the end of the CMI-1 motif), CMI-2 (♦ shows the beginning and the end of the CMI-2 motif), CMI-3 (✱ shows the beginning and the end of the CMI-3 motif) and CMI-4 (* shows the beginning and the end of the CMI-4 motif). The sequences of the AP2/ERF domain and the (CMI-1, CMI-2, CMI-3, CMI-4) motifs of the CpRAP2.4a, CpRAP2.4b proteins were compared to: *Arabidopsis thaliana* (AtRAP2.4a, AtRAP2.4b, AtERF060, AtERF061); *Solanum lycopersicum* (Solyc12g056980); *Selaginella moellendorffii* (Smo_104980); *Oriza sativa* (OS05T0572000, OS02T0752800); *Musa acuminata* (GSMUA_AchrUn_randomP20840, GSMUA_Achr8P28500, GSMUA_Achr5P09470).

DETAILED DESCRIPTION OF THE INVENTION

Figure 2:
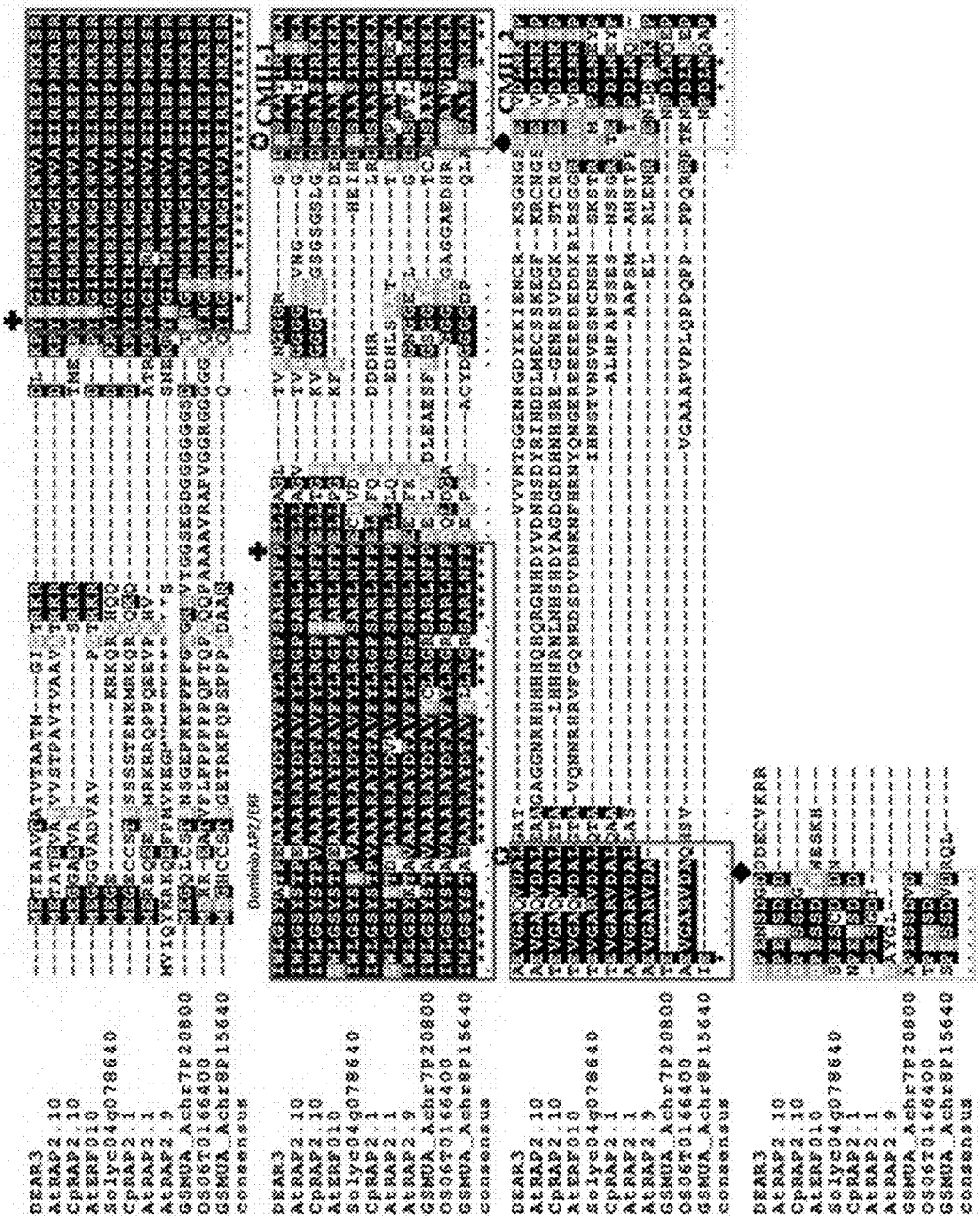
FIG. 2 shows a diagram with multiple alignments of the predicted amino acid sequences of the RAP2.1 and RAP2.10 (group II) proteins, where it can be observed the domain AP2/ERF of *C. papaya* var. Maradol compared to RAP proteins of different related species. The protein sequences were aligned using ClustalW2 and the identity or similarity of amino acids are shown BOXSHADE format. For RAP2.4 individuals the AP2/ERF Domain (✚ shows the beginning and the end of the AP2/ERF domain) and the CMII-1 motifs (○ shows the beginning and the end of the CMI-1motif), CMII-2 (♦ shows the beginning and the end of the CMI-2 motif). The sequences of the AP2/ERF domain and (CMII-1, CMII-2) motifs of the CpRAP2.1 and CpRAP2.10 proteins were compared to: *Arabidopsis thaliana* (DEAR3, AtRAP2.10, AtERF010, AtRAP2.1, AtRAP2.9); *Solanum lycopersicum* (Solyc04g078640); *Oriza sativa* (OS06T0166400); *Musa acuminata* (GSMUA_Achr7P20800, GSMUA_Achr8P15640) and the consensus sequence.

In the hereby invention an alternative is provided to confer resistance or tolerance to abiotic stress due to elevated and low temperatures (extreme temperatures) in plants for periods which have not been previously reported in the state of the art, as well as a method for the generation of transgenic plants and tolerant grafts. The aforementioned is achieved by the application of transcription factors belonging to the RAP2 family isolated from *Carica papaya*, in the hereby invention there have been identified 4 transcription factors and their nucleotide and amino acid sequences, which are called CpRap2.4a, CpRap2.4b, CpRap2.1 and CpRap2.10 genes are provided. The method for the generation of transgenic plants and grafts tolerant to extreme temperatures from the culture of tissues includes specific primers for the isolation of genes, primers for their sub cloning and primers to achieve the overexpression of the CpRap2.4a, CpRap2.4b, CpRap2.1 and CpRap2.10 genes on a binary vector, as well as the transformation method, the selection of plants which are tolerant or resistant to thermal shock and their use as rootstocks for the generation of tolerant grafts.

For understanding better, the hereby invention we are presenting a brief glossary of the terms used:

Elevated temperatures: in the hereby invention it refers to a temperature which is higher than the permissible maximum growth temperature for a given plant species.

Low temperatures: in the hereby invention it refers to a temperature which is lower than the permissible minimum growth temperature for a given plant species.

Thermal shock: in the hereby invention it refers to the sudden elevation of room temperature.

Domain: in the hereby invention it refers to a region of a protein with biological functional or structural interest. It is also considering a region of the tridimensional structure of a protein with a concrete function that includes regions which are not necessarily adjacent in the amino acid sequence.

Abiotic stress: in the hereby invention abiotic stress is the alteration in cellular metabolism induced by abiotic factors, with effect on plant development.

Abiotic factors: in the hereby invention abiotic factors include light, temperature, water, high concentrations of metal and nonmetallic ions and atmospheric pollutants.

Motif: in the hereby invention it refers to the preserved element in the amino acid sequence of a protein, that is habitually associated with a concrete function.

Transgenic plant: in the hereby invention it refers to a genetically modified plant that has one or more sequences of genes artificially introduced, that come from other plants, virus, bacteria or fungi.

Non-transgenic plant: the hereby invention considers as a non-transgenic plant one that has not had an artificial introduction of genes.

Cloning vector: in the hereby invention it refers to carrier molecules that transfer and replicate fragments of DNA.

The process for the development of the invention is described as follows.

Identification and Isolation of the Rap2 Genes Family

Due to the interest of the work team of the hereby invention to identify on *Carica papaya* transcription factors that confer tolerance to abiotic stress in plants, it was proposed to locate the already reported *Carica papaya* var. SunUp genome, those genes related to the Rap2. Family. Thus, it was performed a bioinformatic analysis that is described as follows, thanks to which it was possible to design specific primers that could enable the isolation and identification of the sequences that correspond to the transcription factors matter of the hereby invention.

Design of the Specific Primers to Identify the Rap2 *Carica papaya* Var. Maradol Genes Purpose of the Hereby Invention.

To design specific primers for isolating the genes matter of the hereby invention from *Carica papaya* var. Maradol it was necessary to perform the following activities I to III:

I. To search in the reported literature and in the database of the *Carica papaya* genome about the AP2 super family specifically about the AP2/ERF family.

As first step, it was searched in the literature about this super family of genes, taking as reference what was reported by Nakano T, Suzuki K, Fujimura T, and Shinshi H. (2006). Genome-wide analysis of the ERF gene family in *Arabidopsis* and Rice. *Plant Physiol.* 140:411-432, as well as in the databases of sequence data such as Phytozome, where there are reported sequences of genomes of vegetable species, all of this to identify possible Rap2 genes which are homologue in the genome of the *Carica papaya* var. SunUp.

In Phytozome, there were six complete proteasomes analyzed to relate the families of Rap2 type genes with the ones found in the *Carica papaya* genome. Besides, the sequences from RAP2 proteins were analyzed using the Hidden Markov Model. (HMM, Hidden Markov Model). For the two alignments (Boxshade) the HMM model was built using the HMMER software (version 3.1; Eddy SR 2001). The alignments of the proteasomes were performed in Clustal Omega (Sievers F, Wilm A, Dineen D, Gibson T J, Karplus K, Li W, et al. Fast, scalable generation of high-quality protein multiple sequence alignments using Clustal Omega. *Mol Syst Biol.* 2011; 7: 539) manually run and analyzed with the statistical ProtTest 2.4 package (Abascal F, Zardoya R, Posada D. ProtTest: selection of best-fit models of protein evolution. *Bioinformatics.* 2005; 21: 2104-2105) to locate the best evolutionary model. The resulting (amino acid) of the AP2/ERF domains and the CMI-1, CMI-2, CMI-3 and CMI-4 motifs for the group where the RAP2.4 proteins are represented (group I) as well as of the motifs CMII-1 and CMII-2 where the RAP2.1, RAP2.9 and RAP2.10 (group II) are represented were calibrated with the HMMER v3.1 software. The annotations of the *Arabidopsis thaliana* genome were downloaded from TAIR (The *Arabidopsis thaliana* Information Resource, www.arabidopsis thaliana.org/). The gene files of *Carica papaya* and *Phycomitrella* were taken from Phytozome V.9.0 (www.phytozome.net, Goodstein D M, Shu S, Howson R, Neupane R, Hayes R D, Fazo J, et al. Phytozome: a comparative platform for green plant genomics. *Nucleic Acids Res.* 2012; 40: D1178-1186), *O. sativa japonica* was taken from EnsemblPlants (plants.ensembl.org/index.html, EMBL-EBI). The annotations of *Musa acuminata* were taken from banana-genome.cirad.fr/musa_acuminata, from *Solanum lycopersicum* from www.ebi.ac.uk/ena/data/view/AEKE02000001-AEKE02026877 and from *Selaginella moellendorffii* from www.uniprot.org/proteomes/UP000001514.

The result of the HMM profiles were used to detect RAP2 proteins on files of analyzed proteins. The HMM RAP2 model was fixed with cut-off values. Various sequences of RAP2 proteins were obtained with HMM for group I where RAP2.4 proteins, two sequences of *Physcomitrella patens* (bryophyte), a sequence of *Selaginella moellendorffii* (Lycopodiophyta), six sequences of *Arabidopsis thaliana* (dicotyledonous Magnoliophyta), five sequences of *Solanum lycopersicum* (dicotyledonous Magnoliophyta), seven sequences of *Musa acuminata* (monocotyledonous Magnoliophyta), two sequences of *Oryza sativa* (monocotyledonous Magnoliophyta) and four sequences of *Carica papaya* (dicotyledonous Magnoliophyta are found. For the ones belonging to group II where there are the RAP2.1, RAP2.9 and RAP2.10 proteins, four sequences of *Physcomitrella patens* (bryophyte), eight sequences of *Arabidopsis thaliana* (dicotyledonous Magnoliophyta), three sequences of *Solanum lycopersicum* (dicotyledonous Magnoliophyta, eleven sequences of *Musa acuminata* (monocotyledonous Magnoliophyta), four sequences of *Oryza sativa* (monocotyledonous Magnoliophyta and three sequences of *Carica papaya* (dicotyledoneous Magnoliophyta).

All the sequences were concentrated by CD-HIT with a cut-off value of 0.9 of identity. Because of the phylogenetic analysis there were identified on *Carica papaya* twenty-nine proteins type AP2/ERF from the proteasome of *Carica papaya* var. SunUp inside the files of reported sequences in the Phytozome database, grouping according to the classification reported by Nakano T, Suzuki K, Fujimura T, and Shinshi H. (2006). Genome-wide analysis of the ERF gene family in *Arabidopsis* and Rice. *Plant Physiol.* 140:411-432.

Diverse sequences of *Carica papaya* were selected because they are the closest ones to the RAP2 proteins the ones which were foretold as CpRAP2.4a, CpRAP2.4b, CpRAP2.1 and CpRAP2.10 proteins. The predicted proteins CpRAP2.4a, CpRAP2.4b, CpRAP2.1 and CpRAP2.10 had an identity of 59.7%, 60.2%, 63.9% and 63.5% respectively concerning the proteins already reported in *Arabidopsis thaliana* genome AtERF059, AtERF060, AtERF010 and AtERF011.

II. Alignment of the predicted protein sequences CpRAP2.4a, CpRAP2.4b, CpRAP2.1 and CpRAP2.10 to identify domains and characteristic motifs of the RAP family There were various multiple alignments of the amino acid sequences of the type CpRAP2 of *Carica papaya* proteins, comparing them with RAP proteins of distinct species of related plants. The sequences were aligned using ClustalW2 and the identity or similarity of amino acids were shown on BOXSHADE format (www.ch.embnet.org/software/BOX_form.html). The AP2/ERF domain and the and motifs CMI-1, CMI-2, CMI-3 and CMI-4 for RAP2.4a and RAP2.4b (FIG. 2) as well as the motifs CMII-1 and CMII-2 for RAP2.1 and RAP2.10 (FIG. 2) are identified within the boxes of the two resulting alignments. The sequences of the domains and the typical motifs of the AP2/ERF family on the predicted proteins of CpRAP2.4a, CpRAP2.4b, CpRAP2.1 and CpRAP2.10 were compared to different versions of the proteasomes of *Selaginella moellendorffii, Arabidopsis thaliana, Solanum lycopersicum, Musa acuminata* and *Oryza sativa*. The Boxshade program is characterized for shading alignments on black for identical residues and on gray for similar residues.

Figure 1:
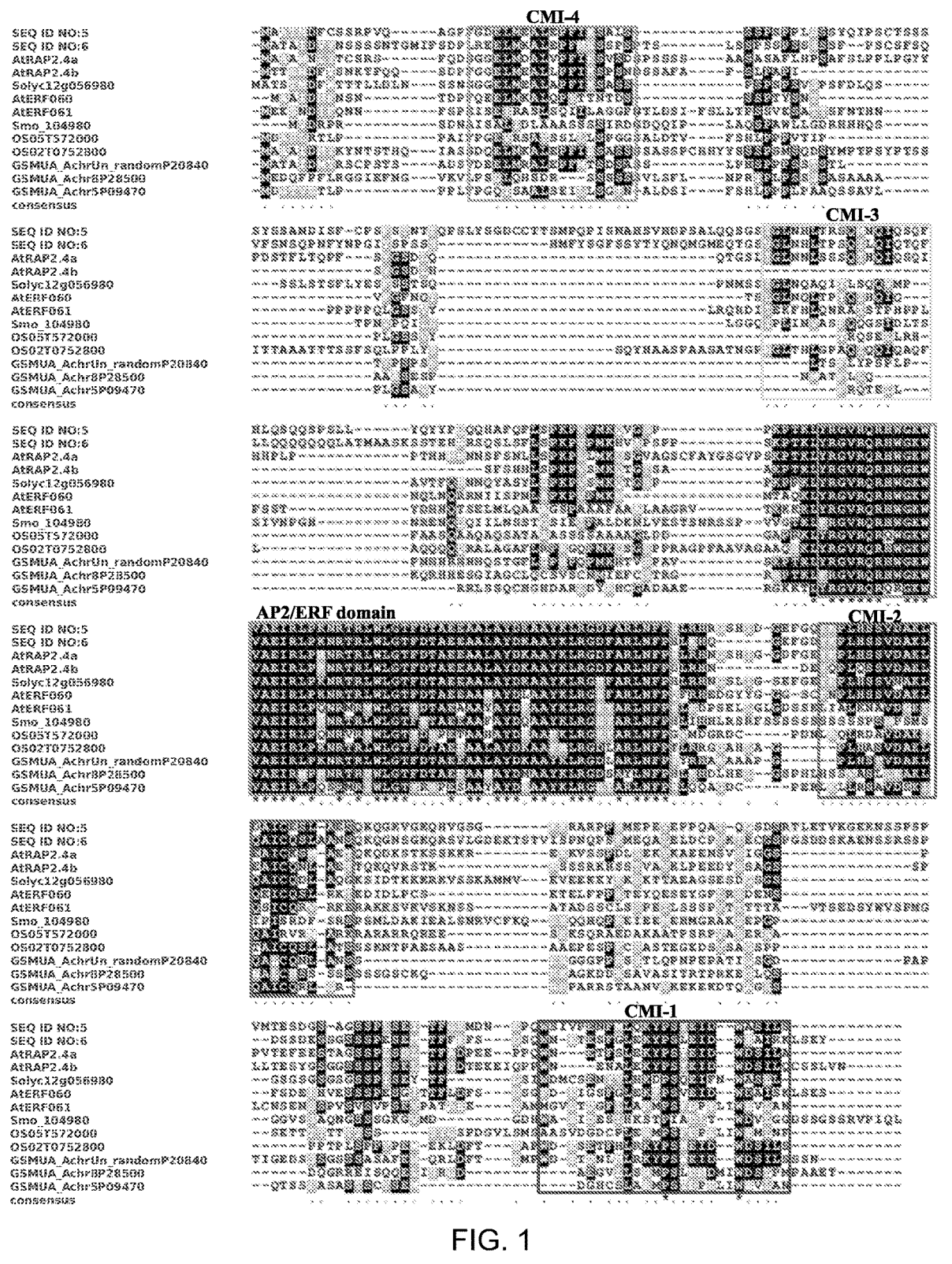

The structural analysis of the predicted proteins CpRAP2.4a and CpRAP2.4b (FIG. 1) showed that the sequences with the domain AP2/ERF and the four motifs CMI: 1, 2, 3 and 4; classified the CpRAP2.4a and CpRAP2.4b proteins within group I according to what was reported by Nakano T, Suzuki K, Fujimura T, and Shinshi H. (2006). Genome-wide analysis of the ERF gene family in *Arabidopsis* and Rice. *Plant Physiol.* 140:411-432.

The alignment analysis of the protein sequences CpRAP2.4a and CpRAP2.4b showed an elevated level of identity of their four motifs compared with the ones of RAP2.4, especially with *Arabidopsis thaliana*. Either motifs CMI: 1, 2, 3 and 4; as well as the AP2/ERF domain show a sequence quite conserved on a specific position. For example, on the AP2/ERF domain (indicated with this symbol ✪ ) is the most conserved area or it is 95% alike in all the species compared to *Carica papaya*.

The structural analysis of the predicted proteins CpRAP2.1 and CpRAP2.10 (FIG. 2) showed that the sequences with the AP2/ERF domain and the two motifs CMII: 1 and 2 classified the CpRAP2.1 and CpRAP2.10 proteins within group II according to what was reported by Nakano T, Suzuki K, Fujimura T, and Shinshi H. (2006). Genome-wide analysis of the ERF gene family in *Arabidopsis* and Rice. *Plant Physiol.* 140:411-432. The alignment analysis of the protein sequences CpRAP2.1 and CpRAP2.10 showed an elevated level of identity of its two motifs compared with the RAP2.1 and RAP2.10 of *Arabidopsis thaliana*. Either the CMII: 1 and 2 motifs as well as the AP2/ERF domain show a quite conserved sequence at a specific sequence.

III. Design of specific primers for isolating and identifying Rap2 gens of *Carica papaya* Maradol var.

Based on the obtained sequences from databases and alignments the complete nucleotide sequences of the predicted genes that codify for the (CpRAP2) proteins were taken, thus initiating the design of specific primers with high levels of astringency, taking the following criteria: 1) each individual primer should include between 18-24 bases; 2) the content of guanines and cytokines was maintained between 40 a 60%; 3) the melting temperature of the "Tm" primers should be between 50 and 65° C.; 4) avoid areas with potentiality to form internal secondary structures or dimers on the primers; 5) to have 100% mating with the CpRap2.4a, CpRap2.4b, CpRap2.1 and CpRap2.10, elected sequences in *Carica papaya*. Thus, the primers known as SEQ ID NO: 9, SEQ ID NO: 10, SEQ ID NO: 13, SEQ ID NO: 14, SEQ ID NO: 17, SEQ ID NO: 18, SEQ ID NO: 21 and SEQ ID NO: 22 originated.

Isolation of the CpRap2.4a, CpRap2.4b, CpRap2.1 and CpRap2.10 Genes of *Carica papaya* Var. Maradol The CpRap2.4a, CpRap2.4b, CpRap2.1 and CpRap2.10 genes were isolated separately of seedlings of *Carica papaya* var. Maradol of eight weeks old, from which it was extracted total RNA from leaves, stem and root using TriZol (Invitrogen, Ca) following the protocol described by the supplier.

A semi quantitative RT-PCR was performed using the SMARTer™ PCR cDNA (Clontech) synthesis kit, from which cDNA was obtained. Later it was used to amplify by PCR each of the CpRap2.4a, CpRap2.4b, CpRap2.1 and CpRap2.10 genes with the primers known as SEQ ID NO: 9 and SEQ ID NO: 10 to amplify the CpRap2.4a gene; SEQ ID NO: 13 and SEQ ID NO: 14 to amplify the CpRap2.4b gene; SEQ ID NO: 17 and SEQ ID NO: 18 to amplify the CpRap2.1 gene; SEQ ID NO: 21 and SEQ ID NO: 22 to amplify the CpRap2.10 gene. Besides control sequences were run.

The PCR product was run on 2% agarose gel, which was isolated and clonated to be sequenced and to corroborate the sequence. The result of the isolation showed us the identification of the CpRap2.4a, CpRap2.4b, CpRap2.1 and CpRap2.10 genes through the sequences called SEQ ID NO: 1, SEQ ID NO: 2, SEQ ID NO: 3 and SEQ ID NO: 4, respectively (view the sequence listing). These sequences were up-loaded to the GenBank with Access numbers: Banklt1869755 (CpRAP2.4a), KU065114, Banklt1869755

(CPRAP2.4b) KU065115, Banklt1869755 (CpRAP2.1) KU065116, Banklt1869755 (CpRAP2.10) KU065117.

Determination of the Expression of the CpRap2.4a, CpRap2.4b, CpRap2.1 and CpRap2.10 Genes Under Abiotic Stress Conditions To determine if the CpRap2.4a, CpRap2.4b, CpRap2.1 and CpRap2.10 genes codify for a transcription factor involved in the signaling that triggers by abiotic stress, the expression patterns of those genes under different stress conditions given by extreme temperatures were determined. For the treatment of abiotic stress seedlings of *Carica papaya* var. Maradol of eight weeks old were used to create a profile of expression of the CpRap2.4a, CpRap2.4b, CpRap2.1 and CpRap2.10 genes under stress conditions for elevated and low temperatures.

For the treatments of stress due to elevated temperatures the papaya seedlings were transferred to a 40° C. chamber, according to Matzukura S., Mizoi J., Yoshida T., Todoka D., Ito Y., Maruyama K., Shinozaki K., Yamaguchi-Shinozaki K. (2010). Comprehensive analysis of rice DREB2-type genes that encode transcription factors involved in the expression of abiotic stress-responsive genes. *Mol Genet Genomics* 283:185-196. For the treatments of low temperatures, the seedlings were maintained at a temperature of 4° C. for two hours. Papaya seedlings at 25° C. were used as control.

The total RNA was extracted from the leaves, stem, sap and roots of the seedlings exposed to elevated and low temperatures (40° C. and 4° C.). Later it was performed a semi quantitative RT-PCR using 1 μg of total RNA and the SMARTer™ PCR cDNA Synthesis Kit (Clontech) kit to evaluate the expression patterns of the CpRap2.4a, CpRap2.4b, CpRap2.1 and CpRap2.10 genes. The obtained cDNA was diluted on a 1:5 proportion and it was used 2 μL of simple at 25 amplification cycles using the SEQ ID NO: 9 and SEQ ID NO: 10 primers to amplify the gene CpRap2.4a; SEQ ID NO: 13 and SEQ ID NO: 14 to amplify the gene CpRap2.4b; SEQ ID NO: 17 and SEQ ID NO: 18 to amplify the gene CpRap2.1 and SEQ ID NO: 21 and SEQ ID NO: 22 to amplify CpRap2.10. As load control, it was used gene 18S to normalize the expression level using universal primers (sense: 5'-CGGCTACCACATC-CAAGGAA-3', antisense: 5'-GCTGGAATTACCGCGGCT-3'). PCR products were run on a 2% agarose gel.

Figure 3:
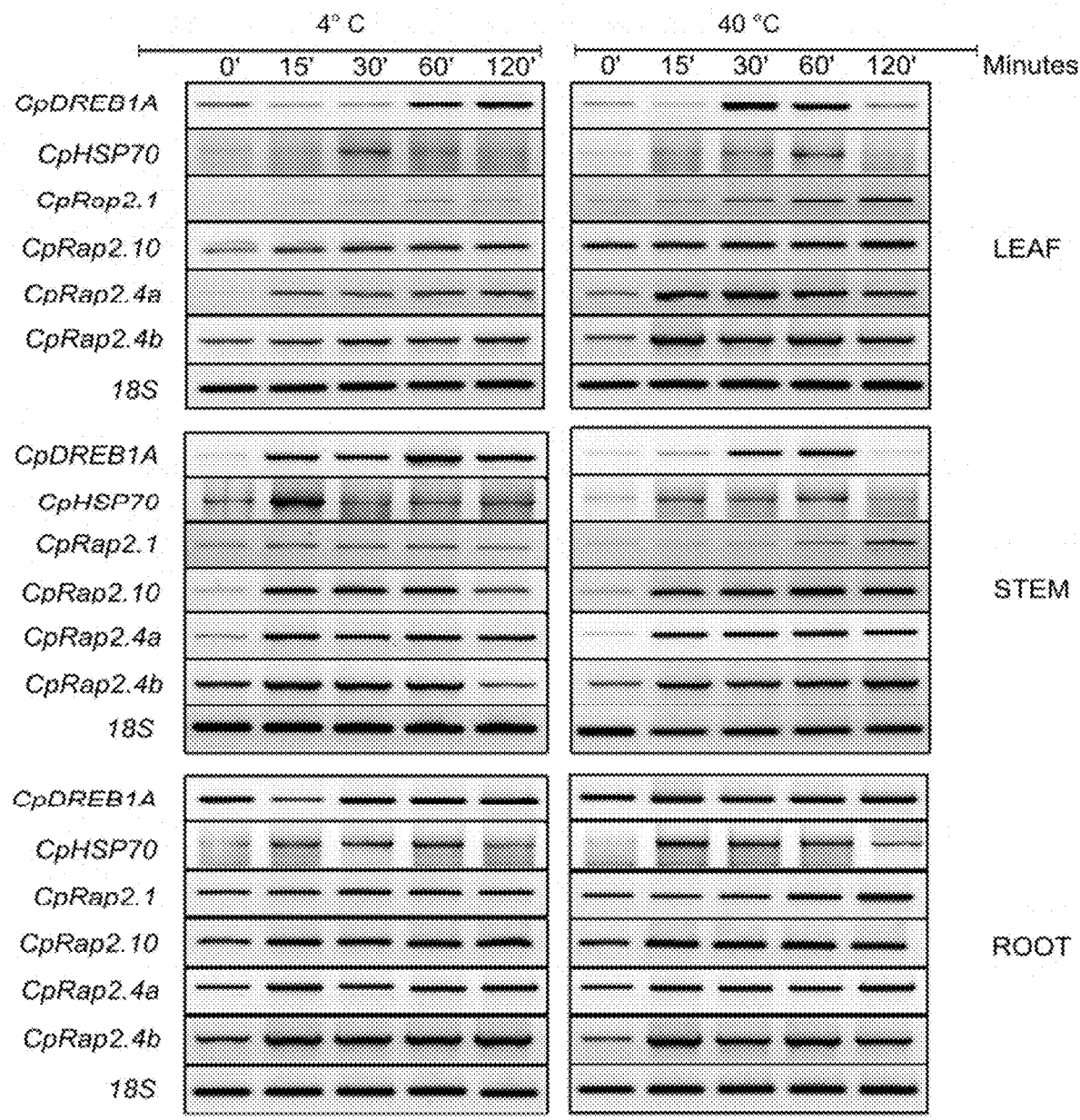
FIG. 3 shows images of agarose gels of the semi quantitative RT-PCR of the expression of the CpRap2.4a, CpRap2.4b, CpRap2.1 and CpRap2.10 genes of seedlings of *Carica papaya* var. Maradol that were subject to extreme temperatures (4° C. and 40° C.) during 2 hours of treatment, on intervals of fifteen, thirty, sixty, one hundred twenty minutes on leaf, stem and root. The quantification of the values of the expression of the CpRap2.4a, CpRap2.4b, CpRap2.1 and CpRap2.10 were normalized with the constitutive gen 18S. As a positive control of the response to extreme temperature the CpDREB1A and CpHSP70 genes that come from *Carica papaya* were used.

The results (FIG. 3) show that the expression of the CpRap2.4a, CpRap2.4b, CpRap2.1 and CpRap2.10 genes was induced in the stress treatments at elevated and low temperatures in a differential manner for the different areas of the plant that were sampled. The accumulation of the transcript of the genes CpRap2.4a, CpRap2.4b, CpRap2.1 and CpRap2.10 was given as a response to stress due to elevated and low temperatures (FIG. 3), there was an increase on the expression 15 minutes after the exposure to treatments. The expression of the genes CpRap2.4a, CpRap2.4b, CpRap2.1 and CpRap2.10 to low temperatures was analyzed and it was observed that the level of expression was strong after two hours of exposure to the treatment, just the same on elevated temperatures, especially on the leaves and on the stem. The results suggest a possible role of the CpRap2.4a, CpRap2.4b, CpRap2.1 and CpRap2.10 genes on the signaling waterfall triggered by abiotic stress.

Figure 4:
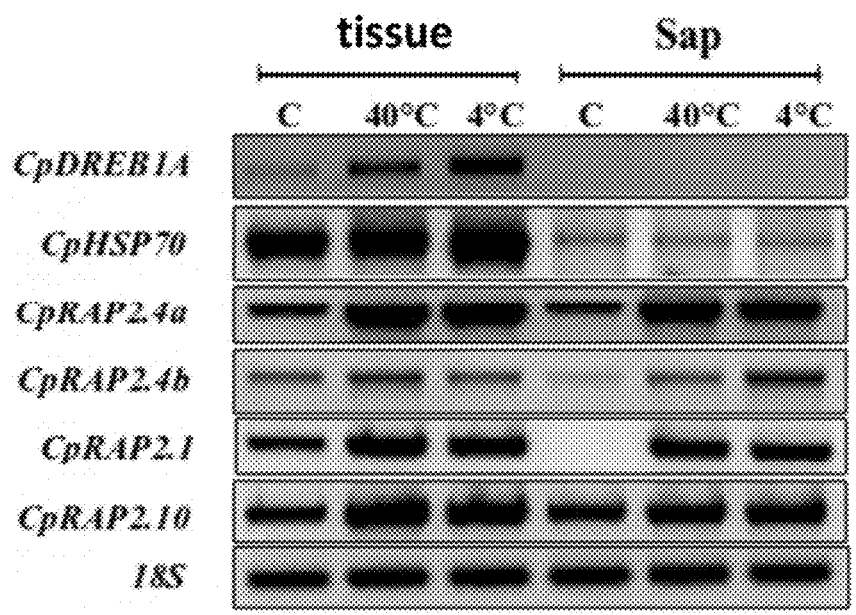
FIG. 4 shows images of agarose gels of semi quantitative RT-PCR of the expression of the CpRap2.4a, CpRap2.4b, CpRap2.1 and CpRap2.10 genes of the tissue and sap of *Carica papaya* var. Maradol seedlings which were subject to 25° C. as control and to stress condition due to extreme temperatures (40° C. and 4° C.) during 2 hours of treatment. Quantification of values of expression of the CpRap2.4a, CpRap2.4b, CpRap2.1 and CpRap2.10 genes were normalized with the constitutive gene 18S. As positive control of the response to extreme temperatures, genes CpDreb1A and CpHsp70 that proceed from *Carica papaya* were used.
Figure 5:
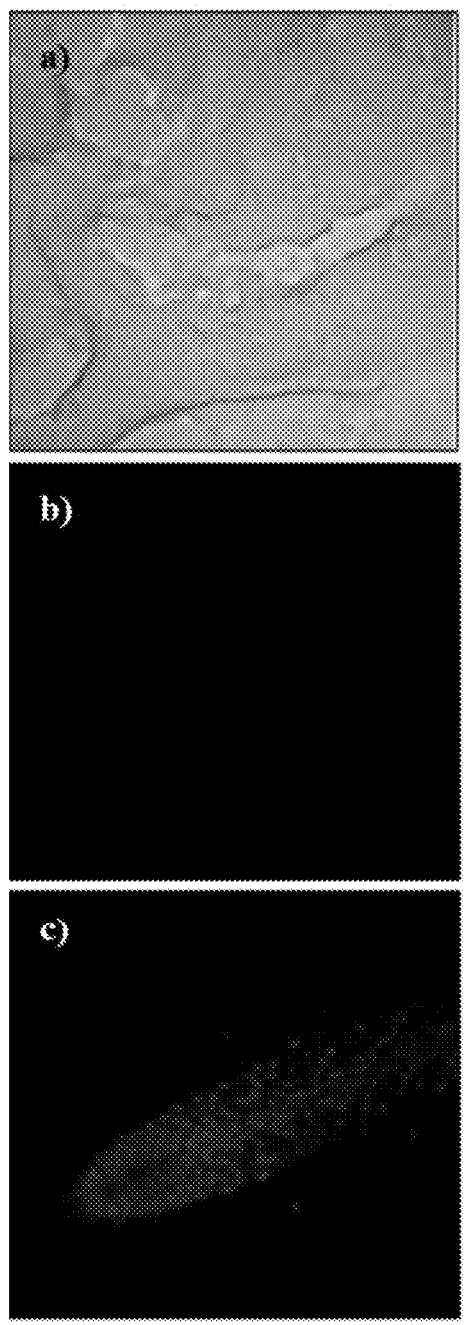
FIG. 5 shows pictures that illustrate the sap of *Carica papaya* recently extracted, observed with light transmitted to the microscope (a) and dyed with DAPI (b) to verify the existence of any trace of nuclear DNA in the sample. Besides a sample of root stained with DAPI (c) to prove that the colorant is confined to the nuclei.
Figure 6:
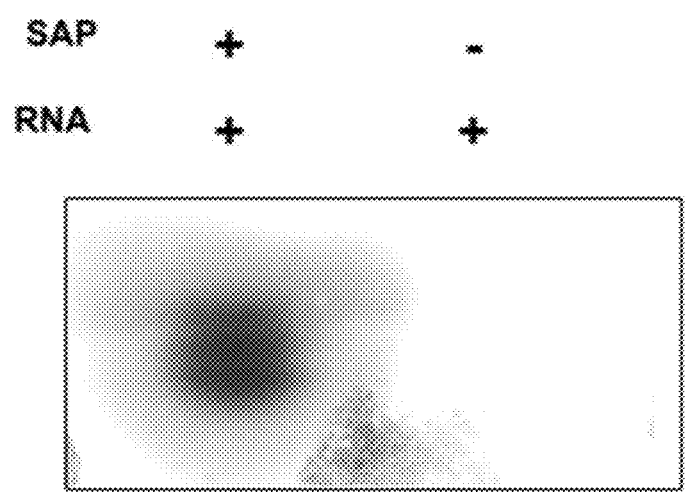
FIG. 6 shows an autoradiography to prove that there is a translation process in the plant phloem a nuclear fibrillarin protein. The experiments were carried out in sap.

Similarly, on sap the expression of the genes CpRap2.4a, CpRap2.4b, CpRap2.1 and CpRap2.10 was differential at temperatures of 4° C. and 40° C., thus demonstrating the presence of Messenger RNA's of the CpRap2.4a, CpRap2.4b, CpRap2.1 and CpRap2.10 genes on sap (FIG. 4). Another way to verify if the sap of the plants has genetic material and that this one does not come from some tissue cores is by means of DAPI staining to sap extracted on which it was observed that extracted sap does not contain cores in the fluorescent microscope (FIG. 5), however it has RNA as it can be seen on FIG. 6.

Generation of Transgenic Plants

Genes like the CpRap2.4a, CpRap2.4b, CpRap2.1 and CpRap2.10 are significant since they confer desirable phenotypic characteristics mainly to plants of commercial interest, which represents a market advantage. For this purpose, they constructed an overexpression vector for each of the aforementioned genes, which can have a fluorescent marker to monitor the transformation. For the generation of transgenic plants of *Nicotiana tabacum* that will overexpress genes CpRap2.4a, CpRap2.4b, CpRap2.1 01 and CpRap2.10 the following process took place:

Construction of Binary Vectors for the Transformation of Each of the CpRap2 Genes.

Starting with isolated genes CpRap2.4a, CpRap2.4b, CpRap2.1 and CpRap2.10 (SEQ ID NO: 1, SEQ ID NO: 2, SEQ ID NO: 3 and SEQ ID NO: 4) the respective binary vectors which express the genes CpRap2.4a, CpRap2.4b, CpRap2.1 and CpRap2.10 of *Carica papaya* var. Maradol were created. This process was carried out by making specific recombination, obtaining each one of the overexpression vectors 35S::CpRap2.4a::GFP, 35S::CpRap2.4b::GFP, 35S::CpRap2.1::GFP and 35S::CpRap2.10::GFP (Example 1). For their replication and conservation, the vectors were introduced in *Escherichia coli*. For the generation of transgenic plants, the vectors were introduced on a strain of *Agrobacterium tumefaciens*.

Transforming and Obtaining Transgenic Plants

For genetic transformation, there were tobacco plants grown in vitro. The plant material was cocultivated with *Agrobacterium tumefaciens* and the selection of transformed plants was carried out with antibiotics. The lines of transgenic plants of *Nicotiana tabacum* that overexpress the genes 35S::CpRap2.4a::GFP, 35S::CpRap2.4b::GFP, 35S::CpRap2.1::GFP and 35S::CpRap2.10::GFP each one on its own, were transferred to potted with substrate until the transgenic seeds were harvested to obtain F1.

Transgenic plants can at the same time be spread through seeds, by cutting, by in vitro cultures and by graft. For the detection of the overexpression of genes CpRap2 on transgenic plants there were diverse techniques used, such as: PCR, RT-PCR, southern blot, dot blot and western blot, using specific primers developed in the hereby invention (SEQ ID NO: 9 and SEQ ID NO: 10 to amplify the gene CpRap2.4a; SEQ ID NO: 13 and SEQ ID NO: 14 to amplify the gene CpRap2.4b; SEQ ID NO: 17 and SEQ ID NO: 18 to amplify the gene CpRap2.1 and SEQ ID NO: 21 and SEQ ID NO: 22 to amplify CpRap2.10).

It was observed that these transgenic plants have the capacity to tolerate abiotic stress when they are subject to extreme temperatures as it is described on example 2.

Generation of Plants Tolerating to Extreme Temperatures Through Grafts

Once transgenic plants were obtained and that it was proven that these expressed desired phenotypic characteristics it was analyzed the possibility to use them as rootstocks to obtain grafts that have the same tolerance to extreme temperatures. In the state of the art it has been described that some transcription factors travel through the phloem, however it still has not been given evidence that indicates the successful obtaining of non-transgenic grafts which are tolerant to extreme temperatures.

The process for the generation of tolerant plants by means of grafts includes the following steps:

I. Generating a transgenic plant that functions as a rootstock. The transgenic rootstock plants are originated following the aforementioned procedures:

II. Selecting the plant that will be grafted.

III. Generating the graft. The graft can be generated by any known technique, for example, cutting the plant that will be grafted at the aerial part, close to an axillary bud (node) giving a tip shape, later the rootstock must also be sectioned making a hole with the shape and size of the graft, and finally they are joined.

EXAMPLES

We are describing in a non-limiting way of the invention, different examples of the uses and applications of the genes CpRap2.4a, CpRap2.4b, CpRap2.1 and CpRap2.10 for conferring tolerance to abiotic stress due to extreme temperatures on cultures with commercial interest.

Example 1: Nicotiana Tabacum Plants that Overexpress Genes CpRap2.4a, CpRap2.4b, CpRap2.1 and CpRap2.10

Nicotiana tabacum plants were transformed using the EHA 105 strain of Agrobacterium tumefaciens and for generating the overexpression vector it was used the pKFWG2.0 vector (Karimi M, Inze D, Depicker A. GATEWAY vectors for Agrobacterium-mediated plant transformation. Trends Plant Sci. 2002; 7: 193-195). From the isolated genes CpRap2.4a, CpRap2.4b, CpRap2.1 and CpRap2.10 (SEQ ID NO: 1, SEQ ID NO: 2, SEQ ID NO: 3 and SEQ ID NO: 4) the respective binary vectors that overexpressed genes CpRap2.4a, CpRap2.4b, CpRap2.1 and CpRap2.10 of Carica papaya var. Maradol were generated. The PCR product of each one of the genes CpRap2.4a, CpRap2.4b, CpRap2.1 and CpRap2.10 was isolated using the KIT CLEAN® GEN II (Q-Biogen). The genes CpRap2.4a, CpRap2.4b, CpRap2.1 and CpRap2.10 of Carica papaya var. Maradol were cloned separately at the vector pGEM-T® Easy (Promega) and later each one of the vectors was separately transformed at the e E. coli XL-Blue strain by the calcium transformation protocol (Sambrook and Russell 2001). The sub-cloning of the genes CpRap2.4a, CpRap2.4b, CpRap2.1 and CpRap2.10 of Carica papaya var. Maradol was performed using the following primers SEQ ID NO: 11 and SEQ ID NO: 12 for the gene CpRap2.4a; SEQ ID NO: 15 and SEQ ID NO: 16 for the gene CpRap2.4b; SEQ ID NO: 19 and SEQ ID NO: 20 for the gene CpRap2.1 and SEQ ID NO: 23 and SEQ ID NO: 24 for the gene CpRap2.10. All the aforementioned primers are used for the recombination since they contain the attB flanking sites for the attP pDONR 221™ (Invitrogen™) site with the help of the Gateway® BP Clonase® (Invitrogen™) for the generation of specific sites to be able to clone all the genes of the binary vector. Later, the genes CpRap2.4a, CpRap2.4b, CpRap2.1 and CpRap2.10 were sub cloned binary vector pKFWG2.0 (Karimi M, Inze D, Depicker A. GATEWAY vectors for Agrobacterium-mediated plant transformation. Trends Plant Sci. 2002; 7: 193-195) that includes the sites attR by recombination using the GATEWAY® LR Clonase®, generating the binary vector pKFWG2.0 that includes the resistance gene to kanamycin (NptII) under the control of the promoter 35S of the cauliflower mosaic virus and the GFP gene, obtaining each one of the overexpression vectors 35S::CpRap2.4a::GFP, 35S::CpRap2.4b::GFP, 35S::CpRap2.1::GFP and 35S::CpRap2.10::GFP. For their replication and conservation, the vectors were introduced in Escherichia coli. For the generation of transgenic plants, the vectors were introduced in an Agrobacterium tumefaciens strain.

For the transformation they were taken as explants leaf discs of Nicotiana tabacum; they were cut using a sterile cork rim (8 mm) and were put on a preculture medium (MS salts MS, 3% of sacarose, 10 ml/L Vitamins B5, 1 mg/L Benzylaminopurine (BAP) and 3 g/L Gelzan). The explants (leaf discs) were incubated at 25° C. under a photoperiod of 16 h light/8 h darkness for 24 h; to be later transformed by the vacuum infiltration method and coculture with Agrobacterium tumefaciens EHA 105 at 25° C. in darkness for 3 days and then they were transferred to a selection medium (salts MS, 3% de sacarose, 10 mL/L Vitamins B5, 1 mg/L Benzylaminopurine (BAP), 0.1 mg/L of NAA, 3 g/L Gelzan, 200 mg/L Thymetiny 150 mg/L de kanamycin) and remained at 25° C. under photoperiod of 16 h light/8 h darkness. In this selection medium the explants remained until complete plants were regenerated and they were then put in potted with a mixture of substrate, peat, agrolite, vermiculite and soil (2:2.2:4) under photoperiod (16 h light/8 h darkness) with a photon flux density of 180 mol m$^2$ s$^{-1}$ to 25° C. until the harvest of transgenic seeds (F0). For the obtention of F1 progeny the seeds obtained from them were sowed in the middle of the selection and the process was repeated until the obtaining of F1 plants.

Example 2. Performance, Location and Expression of Each of the Genes CpRap2.4a, CpRap2.4b, CpRap2.1 and CpRap2.10 in the Tolerance to Abiotic Stress of Extreme Temperatures in the Lines of Transgenic Plants of Nicotiana tabacum For the typification of phenotypes of the four lines of generated transgenic plants from genes CpRap2.4a, CpRap2.4b, CpRap2. and CpRap2.10 described in the hereby invention many tests were required: the first and most important consisted of proving that the four lines of transgenic plants of Nicotiana tabacum that overexpress each one of the genes CpRap2.4a, CpRap2.4b, CpRap2.1 and CpRap2.10 are tolerant to abiotic stress due to extreme temperatures. Later it was determined the location of the expression of the genes CpRap2 in transgenic plants of Nicotiana tabacum by means of histological sections and discoloration of seedlings.

Treatment of Stress Due to Extreme Temperatures

Seeds of transgenic plants of Nicotiana tabacum that overexpress the genes CpRap2 (35S::CpRap2.4a::GFP, 35S::CpRap2.4b::GFP, 35S::CpRap2.1::GFP and 35S::CpRap2.10::GFP) were germinated in a selection medium (salts MS, 3% de sacarose, mL/L Vitamins B5, 200 mg/L timentin, 150 mg/L of kanamycin and 3 g/L Gelzan 10), likewise there were germinated seeds of non transgenic plants using the aforementioned medium except for the timentin and the kanamycin, to generate control plants for treatments. Three weeks later transgenic and non-transgenic seedlings were transferred to a potted mixture with peat, agrolite, vermiculite and soil (2:2:2:4) and grown under photoperiod (16 h light/8 h darkness) with a photon flux density of 180 mol m$^2$ s$^{-1}$ at 25° C. for six weeks. Transgenic plants of Nicotiana tabacum that overexpress the genes CpRap2 (35S::CpRap2.4a::GFP, 35S::CpRap2.4b::GFP, 35S::CpRap2.1::GFP and 35S::CpRap2.10::GFP) and non-transgenic of 42 days old were subject to the following treatments:

Control: plants were watered daily and were maintained at 25° C. (FIGS. 7 and 8).

Figure 7:
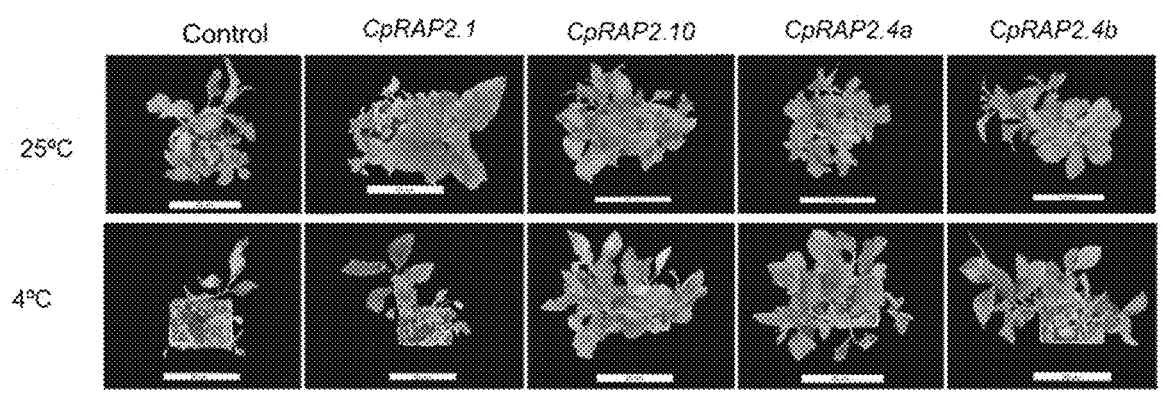
FIG. 7 shows phenotypes of *Nicotiana tabacum* from non-transgenic plants (as control) and transgenic plants that over-express the CpRap2.4a, CpRap2.4b, CpRap2.1 and CpRap2.10 genes subject to room temperature (25° C.) or cold temperature (4° C.) for 30 days of treatment. The plants with over expression of CpRap2.4a, CpRap2.4b, and CpRap2.10 genes have a survival rate of 66.6%, while that plants over expressing of CpRap2.1 has a survival rate of 16.6%.

Low temperatures: plants were subjected to 4° C. for thirty days and watered each two days (FIG. 7).

Figure 8:
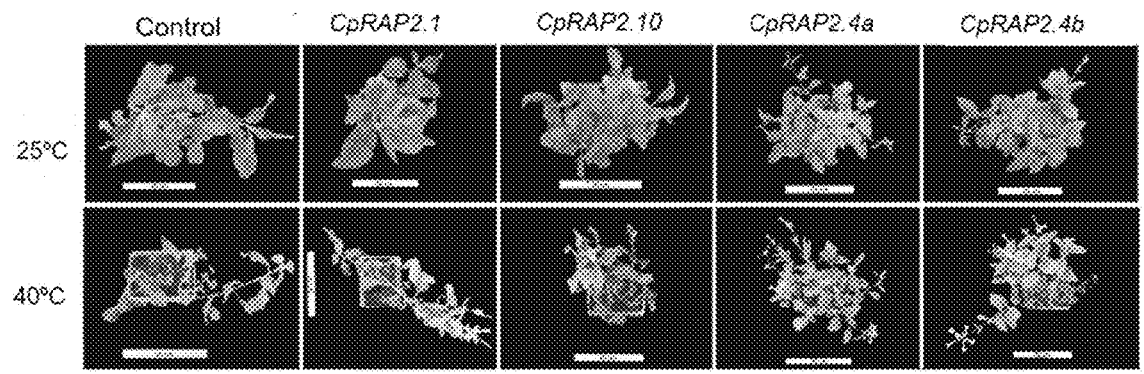
FIG. 8 shows phenotypes of the Non-transgenic *Nicotiana tabacum* plants (as control) and transgenic plants that overexpress CpRap2.4a, CpRap2.4b, CpRap2.1 and CpRap2.10 genes subject to room temperature (25° C.) and extreme heat (40° C.) for 12 days of treatment. The plants with CpRap2.4a gene had a survival rate of 100%. The plants over expressing the CpRap2.4b gene had a survival rate of 50%. Plants over expressing the CpRap2.10 and CpRap2.1 genes had a survival rate of 33.3% and 16.6% respectively.

Elevated temperatures: plants were subjected to 40° C. for twelve days watering them each two days (FIG. 8).

The results show a specific tolerance of transgenic plants of Nicotiana tabacum that overexpress the genes CpRap2 (35S::CpRap2.4a::GFP, 35S::CpRap2.4b::GFP, 35S::CpRap2.1::GFP and 35S::CpRap2.10::GFP) to the treatment due to low temperatures and elevated temperatures (FIGS. 7 and 8), the plants exposed to cold tolerated 30 days of exposure and the plants subjected to heat up to twelve days. The best survival rate on tobacco plants that overexpress the genes CpRap2 was observed for the cold treatment. It was evident that the exposure time of 30 days did not damage most of the transgenic plants notwithstanding the lines used; this means that even when for the line 35S::CpRap2./::GFP there were only two of twelve plants, they weren't totally slaughtered such as happened in the control plants. It is important to mention that lines 35S::CpRap2.4a::GFP, 35S::CpRap2.4b::GFP and 35S::CpRap2.10::GFP had, among them a survival rate like that of cold exposure for 30 days. There were eight out of twelve live plants at the end of the experiment.

In the case of plants subjected to heat the response was different, since plants only survive up to twelve days when exposed to heat; tobacco control plants do not survive to twelve days exposed to heat; however all transgenic lines exposed to this treatment have a favorable response to stress due to heat compared to the control ones, even when the survival levels are variable, it is important to mention that the transgenic line 35S::CpRap2.4a::GFP, had a very encouraging response because out of twelve plants twelve survived to stress of twelve days of heat respect the control line.

To verify that the control plants had died on the heat or cold treatments after the days of exposure we put them back at room temperature under favorable conditions and observed that their impairment was irreversible. However, the surviving transgenic plants kept developing once they were returned to the ideal environmental conditions.

It can be concluded that the transgenic line of plants 35S::CpRap2.4a::GFP was the one that had the best response to exposure to stress due to extreme temperatures in general (FIGS. 7 and 8). Besides, we observed that the flowering process is very quickly induce don those plants treated with extreme heat compared to control plants. In contrast, plants treated with cold had a delay on the floriation process respect control plants. Additionally, we could observe that plants that had already been treated with any of the types of stress, when they were subjected to the stress they had already received, they could more effectively resist to repetitive stress by temperatures.

Cellular Location of the Fluorescence Signal on Transgenic Plants

Figure 9:
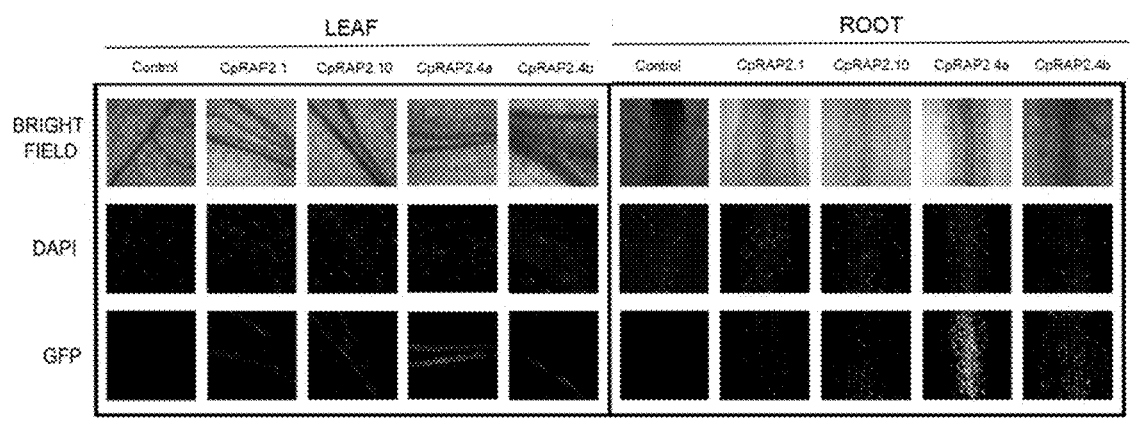
FIG. 9 presents two arrangements of fifteen micrographs each one, to observe the specific tissue behavior of the GFP fused to genes of interest in leaf and root taken at the different longitudes of wave of light established for the detection of DAPI and GFP, as well as micrographs in bright field. The *Nicotiana tabacum* plants that over-express CpRap2.4a, CpRap2.4b, CpRap2.1 and CpRap2.10 genes (35S:CpRAP's:GFP), as well as the (non-transgenic) wild plant as in leaves. The lines that show an important over expression in peripheral cells and conducting vessels as in the root were the lines: CpRap2.4a, CpRap2.4b, CpRap2.10. It is important to point that, for the CpRap2.4a, CpRap2.4b lines, we can see an extra nuclear expression in the roots; concerning the CpRap2.4a line the RAP expression in the ribbings of the leaf is located in sieving elements.

The purpose is to carry out a cellular location analysis, that is, to determine the site where proteins 35S::CpRap2.4a::GFP, 35S::CpRap2.4b::GFP, 35S::CpRap2.1::GFP and 35S::CpRap2.10::GFP are expressing. Transformed plants were faded with alcohol acetic acid for two weeks approximately. Later they were treated with DAPI staining method. The GFP fluorescence (filter excitation of 488 nm, emission band pass filter from 505 to 530 nm) it was analyzed using a laser microscope with focal scan FV100 Olympus. There were non-transgenic plants used as control. The result of the observations (FIG. 9) showed that the fluorescence of tobacco plants with constructions 35S::CpRap2.4a::GFP, 35S::CpRap2.4b::GFP, 35S::CpRap2.1::GFP and 35S::CpRap2.10::GFP was importantly located at the root of the plant line with the construction 35::CpRap2.4a::GFP even though it was also observed an overexpression but with less intensity for the transgenic lines 35S::CpRap2.4b::GFP, 35S::CpRap2.10::GFP and 35S::CpRap2.1::GFP. The same happened for the transgenic line 35S::CpRap2.4a::GFP at the leaf ribs of the tobacco seedlings, because it was observed that the transgenic line had a very strong and particular overexpression in regards with the other transgenic lines; However, for the transgenic lines 35S::CpRap2.4b::GFP, 35S::CpRap2.1::GFP and 35S::CpRap2.10::GFP tit can also be observed a slight overexpression of GFP on sieve elements (FIG. 9). It is important to point out that the expression of the GFP of the transcription factors is expected to be exclusively in the core; However, we can see that for the case of the transgenic line 35S::CpRap2.4a::GFP the expression is also extra-nuclear. These results supported the idea of using these plants as rootstocks.

Presence of Genes CpRap2 and NptII in Transgenic Plants

To verify the presence of genes CpRap2 and NptII in transgenic plants (F0 and F1) the extraction of gDNA using 0.5 g of leaves and mixing them with extraction buffer (0.1 M Tris-HCl, pH8.0; 0.02 M EDTA, pH 8.0; 2% (p/v) CTAB; 2% (p/v) Polyvinylpyrrolidone-40; 0.2% 2-mercaptoethanol), the sample was incubated for an hour at 70° C. The aqueous solution was added equal volumes of chloroform: isoamyl alcohol (24:1, v/v) and centrifuged at 15,000×g at 4° C. for 10 minutes. The aqueous phase was transferred to a new tube and the genetic material was precipitated with an equal volume of isopropanol. The sample was subjected to a temperature of −80° C. for 1 h. The precipitated genetic material was washed with an ethanol solution at 80% and finally the DNA was dissolved in ultrapure water. For the PCR test, the primers of the genes CpRap2.4a, CpRap2.4b, CpRap2.1 and CpRap2.10 were used (SEQ ID NO: 9 and SEQ ID NO: 10 to amplify the CpRap2.4a gene, SEQ ID NO: 13 and SEQ ID NO: 14 to amplify the CpRap2.4b gene, SEQ ID NO: 17 and SEQ ID NO: 18 to amplify the CpRap2.1 gene and SEQ ID NO: 21 and SEQ ID NO: 22 to amplify CpRap2.10), as well as the primers for the gene NptII sense primer (5'-ATGATTGAACAAGATGGATTGC-3') and antisense primer (5'-TCAGAAGAACTCGT-CAAGAAGG-3') to confirm the transformation of the tissue. For comparison effects, it was also extracted genetic material from a non-transgenic plant of Nicotiana tabacum which was used as experiment control. The results were observed on an agarose gel at 1.5% which was stained with ethidium bromide, where it was clearly observed the amplification of PCR products in transgenic plants of Nicotiana tabacum identifying fragments of approximately 855 pb for CpRap2.4a, 1146 pb for CpRap2.4b, 1474 pb for CpRap2.1 and 546 pb para CpRap 2.10, as well as the amplification product of the gene NptII with a 750 pb size, thus corroborating that the primers that were used (SEQ ID NO: 9 and SEQ ID NO: 10 to amplify the gene CpRap2.4a; SEQ ID NO: 13 and SEQ ID NO: 14 to amplify the gene CpRap2.4b; SEQ ID NO: 17 and SEQ ID NO: 18 to amplify the gene CpRap2.1 and SEQ ID NO: 21 and SEQ ID NO: 22 to amplify CpRap2.10) amplify highly specific sequences and do not amplify any sequence on Nicotiana tabacum.

Example 3. Essay to Verify the Long-Distance Movement and Functionality of Transcription Factors CpRap2 Through Grafts The first step on this experiment was to make the grafts. It was worked with transgenic and non-transgenic plants of 30-40 days old; each one of the plants was subjected to an approximate "V" cut at the middle of the plant complementary or cleft to hold the rootstock of the graft. To hold the rootstock a mooring with Parafilm® was made, making sure the ends to be joined were firm. Tests of movement and functionality were carried out 20 days after making the graft. The analysis of presence and absence of genes was performed before and after the graft process. A PCR was performed to prove that non-transgenic plants which would undergo grafting did not have the presence of the gene NptII or the gene CpRap2.4a; likewise, there were also PCR tests on transgenic plants CpRap2.4a to verify the transgenic line includes the presence of the NptII gene and the transgene CpRap2.4a.

Figure 10:
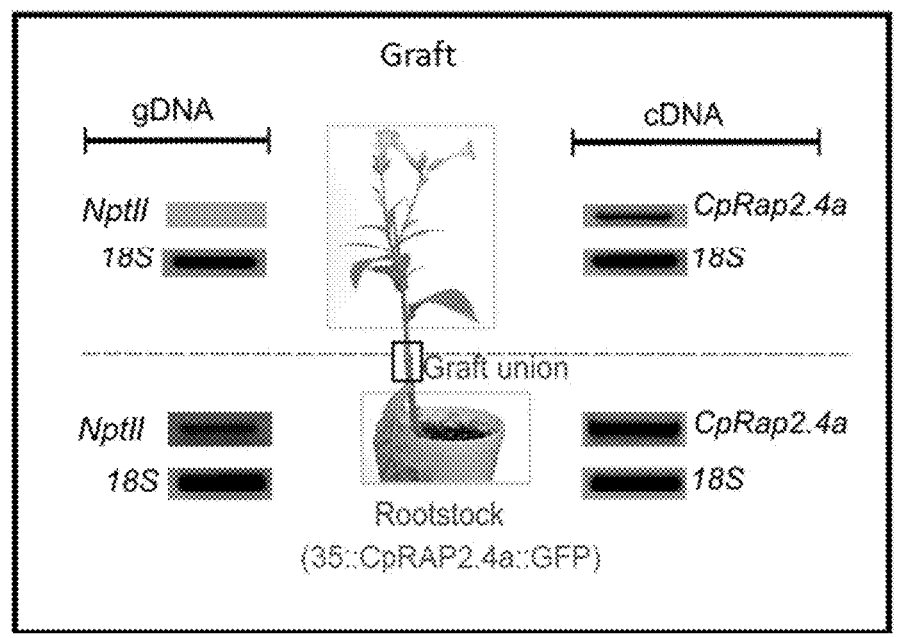
FIG. 10 shows an outline of a grafted plant where the pattern or rootstock is a transgenic tobacco plant (35S::CpRAP's::GFP) and the top or graft is a non-transgenic plant (Non-transgenic stem). On this outline, it can be seen through a PCR on a genomic DNA (gDNA) the presence of the NptII gene in the rootstock and its absence in the graft, and on the other hand it can be seen in the complementary DNA (cDNA) obtained from a RT-PCR the specific gene CpRap2.4a over expressed in the rootstock and in the graft, thus showing that the messenger RNA migrated from CpRap2.4a a through the graft. Gen 18S was used as control.
Figure 11:
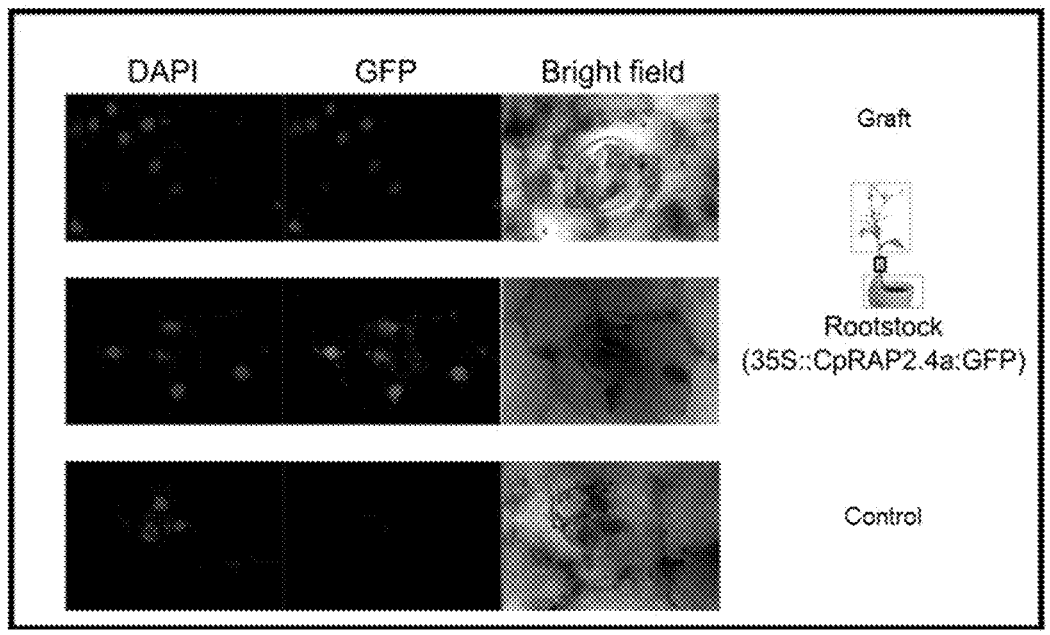
FIG. 11 shows patterns of sub cellular and nuclear accumulation of the CpRAP2.4 protein merged to GFP on a tobacco graft through photographs taken at the different wavelengths of light established for the detection of DAPI and GFP, as well as micrographs in clear field. At the top horizontal line, it can be proven the location of the CpRAP2.4a protein merged to a GFP for the graft (non-transgenic graft), in the middle horizontal line it can be proven the location of the same construction in the (Rootstock) pattern and in the lower horizontal line it can be seen the location of the DAPI of the (non-transgenic) control plant.
Figure 12:
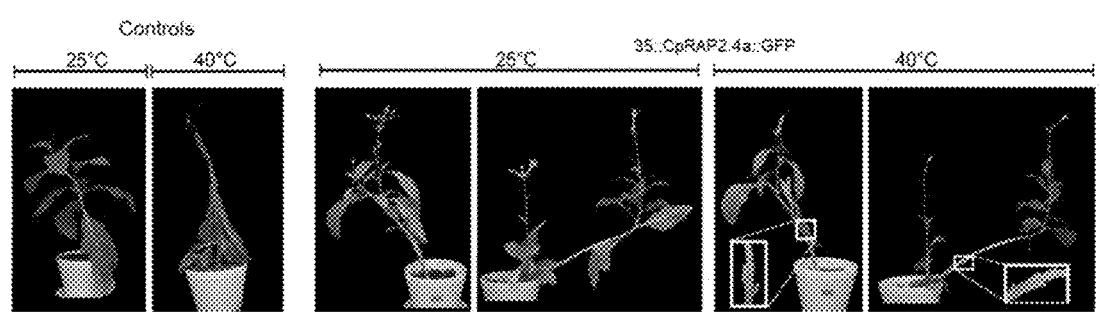
FIG. 12 shows the phenotype of transgenic plants of tobacco (35S::CpRAP2.4a::GFP) and their non-transgenic grafts in response to the stress due to elevated temperature (40° C.) as well as at room temperature (25° C.). Wild tobacco (non-transgenic) Wild tobacco plants (Non-transgenic) were used as controls.

On FIG. 10, that shows PCR products we can clearly observe that the grafted plant (non-transgenic plant) has the presence of the RNA messenger of the transgene CpRap2.4a and it lacks the presence of the resistance gene to kanamycin NptII, concluding with these results that the RNA messengers of the trans gene CpRap2.4a and protein can travel through the phloem and confer properties such as tolerance to extreme temperatures on the grafted plant, overall the products of these grafted plants are not transgenic. Another way for verifying the presence of over expression of the gene CpRap2.4a on the graft was by means of confocal fluorescence micrograph where it was observed the presence of the GFP fused protein at the construction 35::CpRap2.4a:: GFP on the grafted plant (FIG. 11). Since it was shown the presence of the over expression of the gene CpRap2.4a by PCR and by microscope at the grafted plant, the last thing to demonstrate was the tolerance of the grafted plant to extreme temperatures. FIG. 12 shows the response of a non-transgenic tobacco plant and a grafted plant subjected to elevated temperatures (40° C.) for a period of 12 days, where it is demonstrated that the grafted plant acquires the capacity to tolerate elevated temperatures for 12 days, characteristics that are not of a non-transgenic plant since after 12 days of been at 40° C. they do not survive.

For all the above it can be concluded that intercellular communication is a crucial process in plants since thanks to it they can respond to any change in their environment and can adapt to almost any stress condition. Transcription factors are very important proteins in the plant signaling waterfall since once they are activated by various molecules or second messengers (MAPK's, ubiquitination, etc.) they can regulate a specific stress. However, not all of them have the capacity to travel through the phloem of plants as the transcription factors CpRAP2.4a, CpRAP2.4b, CpRAP2.1 and CpRAP10. Transcription factors CpRAP2.4a, CpRAP2.4b, CpRAP2.1 and CpRAP10 give instructions directly to the DNA to determine the type of molecules required to face external changes. So, implementing these transcription factors on grafted plants of economic importance is an alternative for the tolerance to extreme temperatures, with the obtaining of a non-transgenic product.

The invention claimed is:

1. A plant transgenically expressing SEQ ID NO: 5.

2. The plant according to claim 1, wherein the plant comprises a transgenic rootstock.

3. A plant tissue or plant cell transgenically expressing SEQ ID NO: 5.

4. A non-transgenic graft for obtaining a graft wherein a rootstock is a plant according to claim 1.

5. A method for obtaining a non-transgenic graft comprising:
 a) providing a transgenic rootstock,
 b) choosing a plant that will be grafted,
 c) generating a graft of the selected plant in the rootstock, wherein the transgenic rootstock is a plant according to claim 1.

* * * * *

SEQUENCE LISTING

```
<160> NUMBER OF SEQ ID NOS: 24

<210> SEQ ID NO 1
<211> LENGTH: 855
<212> TYPE: DNA
<213> ORGANISM: Carica papaya

<400> SEQUENCE: 1
atgcctcaac ctatttcaaa cgcgcactcg gttcatgatc cgtcggctct ccagcaatcg      60
gggtcgatcg ggctgaatca cctcactcgg tctcagatga accagatcca gtcgcaattt     120
cacctccaga gtcaacaaag cccgtcttta ctgtaccaat attatcctca acagcagcat     180 gccttcagt tcctcagccc aaagcctgtt ccaatgaagc aagttggttc ccccccaaag     240
cccaccaagc tctacagggg tgtgaggcag cggcattggg gcaagtgggt cgccgagatc     300
cgcctgccga agaaccggac ccggctttgg ctcggcacct tcgatacggc cgaggaagca     360
gccttagctt acgacaaggc agcttacaag ctccgaggtg acttcgctcg gctcaacttc     420
cccaatctcc gccaccgggg atcccacatc gacggcgagt tcggccagta caagcccctt     480
cattcctcag tggacgcaaa gcttgatgct atctgtgaaa gtttagcaga gtcgcagaag     540
caggggaaag tggggaagca acatgttggc tccggcaaga agcgagccag gcctcctcgt     600
atggagccag aggttgagcc accgcaggct atacaaggtt cagattcgag aacgttagag     660
acggttaagg gcgagaagaa ttcctccccg tcgccggtga tgaccgagag cgatgggtct     720
gcaggatctt cacctttatc cgagatcacg ttcggtgaaa tggacaacga gccgcagtgg     780
agtattgtgc cggagaactt catgttgcag aagtaccctt catacgagat cgattgggcc     840
tccatattgt catga                                                      855

<210> SEQ ID NO 2
<211> LENGTH: 1146
```

```
<212> TYPE: DNA
<213> ORGANISM: Carica papaya

<400> SEQUENCE: 2
atggcaacag ctatagatgt gtataatagt agcagcagca acacaggcat gattttctca      60
gatcctctga gaagagagct catgaaagca ctggaacctt ttatgaaaag ttctccatct     120
ccaacttctc tctcttctcc ttcttcccca tcttcttctt cctctttccc ttcttgctct     180
ttctctcaag tcttttccaa ttctcagccc aatttctaca atcctggtat ttactcccca     240
tcgagctccc acatgtttta cagtgggttc tcgagctaca cctaccaaaa tcaaatgggt     300
atggagcaaa caggatcggt tgggctcaat caccttactc catctcaaat tctgcaaatc     360
caaactcaat ttctccttca acaacaacaa cagcagcagc tagccaccat ggcagcatct     420
aaatcatcaa cggaacataa ccggagccag agcctgagct ttctctcccc aaaacctgtt     480
cccatgaagc atgttgctcc ttctcctccg tcaaagccca cgaagcttta cagaggagtg     540
aggcagaggc actggggcaa atgggtggcc gagatcagac tccccaagaa ccgtacccgt     600
ctatggctcg gcacttttga cacggcggag gaggctgctc tggcttacga caaggcggca     660
tacaagcttc gtggagactt cgcgaggctc aactttcccc atctcaagca ccaaggcgag     720
ttcggcgact acaagcccct tcattcctct gttgacgcta agctccaagc catctgtcaa     780
agcttggctg ccaattctca aaaacagggg aactctggga agcaaggtc tgttctcggc      840 gatgaaaaga cctcgaccgt aatatctccg aatcagccgt cgaagatgga gcaggcgctt     900
gaactggatt gtccggtgaa gactgaatgt gggtctccgg gatcggatga ttcgaaggcg     960
gaaaactcat caagatcatc gccagattca tccgacgagt cctctggttc gtcatcccct    1020
gaatcagaaa tgactttctt tgaattctct gattcgcagt ggaacgagac agagagcttc    1080
ggattagaga agtacccatc gttggagatt gattgggaag ctataaggaa actatccgaa    1140
tattaa                                                              1146

<210> SEQ ID NO 3
<211> LENGTH: 474
<212> TYPE: DNA
<213> ORGANISM: Carica papaya

<400> SEQUENCE: 3
atggaaggag agtgttgttc gacgacgagc agtagcagca cagagaacaa gatgagaaag      60
cagagacagc agaagcaaga taagccgtac aggggatca ggatgaggaa gtggggtaag      120
tgggtggcgg agatcagaga acccaacaag cgttccagga tctggctcgg ctcttactcc     180 accccgtcg ccgccgctcg cgcctacgac accgccgtct tctacctccg tggtccatcc      240
gccagactca acttcccgga actcgtcttc caagacgacg acgatcatcg cctccgtgac     300
atgtctgccg catccatacg caagaaggcc acggaggtcg gcgccagagt tgacgcactc     360
caggctgcgg ctctccaccc cgcaccttcc tccgagtcca actcttccgg acgggtaacc     420
gagaaacccg acttgaacga gtacccgaat ccggaaactt ccgatgaaga ctga           474

<210> SEQ ID NO 4
<211> LENGTH: 486
<212> TYPE: DNA
<213> ORGANISM: Carica papaya

<400> SEQUENCE: 4
atggagggtg gagcggaggt cgcgagttcg aggaagagga cgatggagcg gccgtacaag       60
```

-continued

```
tcaaggattt ggctcggctc atattcaacc cctgtcgcgg cggctcgggc gtatgacacg    120
gccgtcttct accttagggg acccaccgcc aggctcaact cccagagct cctcacgggg    180 gagaaagtca gcggaggagg catcggcggg ggatctggct caggctcgtt aggcggcgat    240
atgtcagccg cttccataag gaaaaaagcc accgaggtcg gcgcgcaagt cgacgcgctg    300
gaaactgctc tccatcacca ccgtaaccttt aatcacagcc acgattacgc cggcgatggc    360
cgagatcata atcacagccg ggaaggtgaa aataggtcag tggatggcaa gagcacttgc    420
cgcgggttat tggagcgggt tgacttgaat aagataccag acccagatag ttcggatggc    480
gagtga                                                                486
```

<210> SEQ ID NO 5
<211> LENGTH: 284
<212> TYPE: PRT
<213> ORGANISM: Carica papaya

<400> SEQUENCE: 5

```
Met Pro Gln Pro Ile Ser Asn Ala His Ser Val His Asp Pro Ser Ala
1               5                   10                  15

Leu Gln Gln Ser Gly Ser Ile Gly Leu Asn His Leu Thr Arg Ser Gln
            20                  25                  30

Met Asn Gln Ile Gln Ser Gln Phe His Leu Gln Ser Gln Gln Ser Pro
        35                  40                  45

Ser Leu Leu Tyr Gln Tyr Tyr Pro Gln Gln Gln His Ala Phe Gln Phe
    50                  55                  60

Leu Ser Pro Lys Pro Val Pro Met Lys Gln Val Gly Ser Pro Pro Lys
65                  70                  75                  80

Pro Thr Lys Leu Tyr Arg Gly Val Arg Gln Arg His Trp Gly Lys Trp
                85                  90                  95

Val Ala Glu Ile Arg Leu Pro Lys Asn Arg Thr Arg Leu Trp Leu Gly
            100                 105                 110

Thr Phe Asp Thr Ala Glu Glu Ala Ala Leu Ala Tyr Asp Lys Ala Ala
        115                 120                 125

Tyr Lys Leu Arg Gly Asp Phe Ala Arg Leu Asn Phe Pro Asn Leu Arg
    130                 135                 140

His Arg Gly Ser His Leu Asp Gly Glu Phe Gly Gln Tyr Lys Pro Leu
145                 150                 155                 160

His Ser Ser Val Asp Ala Lys Leu Asp Ala Ile Cys Glu Ser Leu Ala
                165                 170                 175

Glu Ser Gln Lys Gln Gly Lys Val Gly Lys Gln His Val Gly Ser Gly
            180                 185                 190

Lys Lys Arg Ala Arg Pro Pro Arg Met Glu Pro Glu Val Glu Pro Pro
        195                 200                 205

Gln Ala Ile Gln Gly Ser Asp Ser Arg Thr Leu Glu Thr Val Lys Gly
    210                 215                 220

Glu Lys Asn Ser Ser Pro Ser Pro Val Met Thr Glu Ser Asp Gly Ser
225                 230                 235                 240

Ala Gly Ser Ser Pro Leu Ser Glu Ile Thr Phe Gly Glu Met Asp Asn
                245                 250                 255

Glu Pro Gln Trp Ser Ile Val Pro Glu Asn Phe Met Leu Gln Lys Tyr
            260                 265                 270

Pro Ser Tyr Glu Ile Asp Trp Ala Ser Ile Leu Ser
        275                 280
```

```
<210> SEQ ID NO 6
<211> LENGTH: 381
<212> TYPE: PRT
<213> ORGANISM: Carica papaya

<400> SEQUENCE: 6

Met Ala Thr Ala Ile Asp Val Tyr Asn Ser Ser Ser Asn Thr Gly
1               5                   10                  15

Met Ile Phe Ser Asp Pro Leu Arg Glu Glu Leu Met Lys Ala Leu Glu
            20                  25                  30

Pro Phe Met Lys Ser Ser Pro Ser Pro Thr Ser Leu Ser Ser Pro Ser
                35                  40                  45

Ser Pro Ser Ser Ser Ser Ser Phe Pro Ser Cys Ser Phe Ser Gln Val
        50                  55                  60

Phe Ser Asn Ser Gln Pro Asn Phe Tyr Asn Pro Gly Ile Tyr Ser Pro
65                  70                  75                  80

Ser Ser Ser His Met Phe Tyr Ser Gly Phe Ser Ser Tyr Thr Tyr Gln
                85                  90                  95

Asn Gln Met Gly Met Glu Gln Thr Gly Ser Val Gly Leu Asn His Leu
                100                 105                 110

Thr Pro Ser Gln Ile Leu Gln Ile Gln Thr Gln Phe Leu Leu Gln Gln
                115                 120                 125

Gln Gln Gln Gln Gln Leu Ala Thr Met Ala Ala Ser Lys Ser Ser Thr
130                 135                 140

Glu His Asn Arg Ser Gln Ser Leu Ser Phe Leu Ser Pro Lys Pro Val
145                 150                 155                 160

Pro Met Lys His Val Ala Pro Ser Pro Ser Lys Pro Thr Lys Leu
                165                 170                 175

Tyr Arg Gly Val Arg Gln Arg His Trp Gly Lys Trp Val Ala Glu Ile
                180                 185                 190

Arg Leu Pro Lys Asn Arg Thr Arg Leu Trp Leu Gly Thr Phe Asp Thr
                195                 200                 205

Ala Glu Glu Ala Ala Leu Ala Tyr Asp Lys Ala Ala Tyr Lys Leu Arg
210                 215                 220

Gly Asp Phe Ala Arg Leu Asn Phe Pro His Leu Lys His Gln Gly Glu
225                 230                 235                 240

Phe Gly Asp Tyr Lys Pro Leu His Ser Ser Val Asp Ala Lys Leu Gln
                245                 250                 255

Ala Ile Cys Gln Ser Leu Ala Ala Asn Ser Gln Lys Gln Gly Asn Ser
                260                 265                 270

Gly Lys Gln Arg Ser Val Leu Gly Asp Glu Lys Thr Thr Val Ile
                275                 280                 285

Ser Pro Asn Gln Pro Ser Lys Met Glu Gln Ala Leu Glu Leu Asp Cys
                290                 295                 300

Pro Val Lys Thr Glu Cys Gly Ser Pro Gly Ser Asp Ser Lys Ala
305                 310                 315                 320

Glu Asn Ser Ser Arg Ser Ser Pro Asp Ser Asp Glu Ser Ser Gly
                325                 330                 335

Ser Ser Ser Pro Glu Ser Glu Met Thr Phe Phe Glu Phe Ser Asp Ser
                340                 345                 350

Gln Trp Asn Glu Thr Glu Ser Phe Gly Leu Glu Lys Tyr Pro Ser Leu
                355                 360                 365

Glu Ile Asp Trp Glu Ala Ile Arg Lys Leu Ser Glu Tyr
                370                 375                 380
```

<210> SEQ ID NO 7
<211> LENGTH: 157
<212> TYPE: PRT
<213> ORGANISM: Carica papaya

<400> SEQUENCE: 7

Met Glu Gly Glu Cys Cys Ser Thr Thr Ser Ser Ser Thr Glu Asn
1               5                   10                  15

Lys Met Arg Lys Gln Arg Gln Lys Gln Asp Lys Pro Tyr Arg Gly
            20                  25                  30

Ile Arg Met Arg Lys Trp Gly Lys Trp Val Ala Glu Ile Arg Glu Pro
            35                  40                      45

Asn Lys Arg Ser Arg Ile Trp Leu Gly Ser Tyr Ser Thr Pro Val Ala
50                      55                  60

Ala Ala Arg Ala Tyr Asp Thr Ala Val Phe Tyr Leu Arg Gly Pro Ser
65                  70                  75                  80

Ala Arg Leu Asn Phe Pro Glu Leu Val Phe Gln Asp Asp Asp His
                85                  90                  95

Arg Leu Arg Asp Met Ser Ala Ala Ser Ile Arg Lys Lys Ala Thr Glu
            100                 105                 110

Val Gly Ala Arg Val Asp Ala Leu Gln Ala Ala Ala Leu His Pro Ala
            115                 120                 125

Pro Ser Ser Glu Ser Asn Ser Ser Gly Arg Val Thr Glu Lys Pro Asp
    130                 135                 140

Leu Asn Glu Tyr Pro Asn Pro Glu Thr Ser Asp Glu Asp
145                 150                 155

<210> SEQ ID NO 8
<211> LENGTH: 181
<212> TYPE: PRT
<213> ORGANISM: Carica papaya

<400> SEQUENCE: 8

Met Glu Gly Gly Ala Glu Val Ala Ser Ser Arg Lys Arg Thr Met Glu
1               5                   10                  15

Arg Pro Tyr Lys Gly Ile Arg Met Arg Lys Trp Gly Lys Trp Val Ala
            20                  25                  30

Glu Ile Arg Glu Pro Asn Lys Arg Ser Arg Ile Trp Leu Gly Ser Tyr
            35                  40                  45

Ser Thr Pro Val Ala Ala Ala Arg Ala Tyr Asp Thr Ala Val Phe Tyr
    50                  55                  60

Leu Arg Gly Pro Thr Ala Arg Leu Asn Phe Pro Glu Leu Leu Thr Gly
65                  70                  75                  80

Glu Lys Val Ser Gly Gly Ile Gly Gly Ser Gly Ser Gly Ser
            85                  90                  95

Leu Gly Gly Asp Met Ser Ala Ala Ser Ile Arg Lys Lys Ala Thr Glu
            100                 105                 110

Val Gly Ala Gln Val Asp Ala Leu Glu Thr Ala Leu His His Arg
            115                 120                 125

Asn Leu Asn His Ser His Asp Tyr Ala Gly Asp Gly Arg Asp His Asn
    130                 135                 140

His Ser Arg Glu Gly Glu Asn Arg Ser Val Asp Gly Lys Ser Thr Cys
145                 150                 155                 160

Arg Gly Leu Leu Glu Arg Val Asp Leu Asn Lys Ile Pro Asp Pro Asp
                165                 170                 175

-continued

Ser Ser Asp Gly Glu
        180

<210> SEQ ID NO 9
<211> LENGTH: 23
<212> TYPE: DNA
<213> ORGANISM: Carica papaya

<400> SEQUENCE: 9
atgcctcaac ctatttcaaa cgc                                          23

<210> SEQ ID NO 10
<211> LENGTH: 23
<212> TYPE: DNA
<213> ORGANISM: Carica papaya

<400> SEQUENCE: 10
tcatgacaat atggaggccc aat                                          23

<210> SEQ ID NO 11
<211> LENGTH: 41
<212> TYPE: DNA
<213> ORGANISM: Carica papaya

<400> SEQUENCE: 11
aaaaagcagg cttcaccatg ctctaaccta tttcaaactc g                      41

<210> SEQ ID NO 12
<211> LENGTH: 37
<212> TYPE: DNA
<213> ORGANISM: Carica papaya

<400> SEQUENCE: 12
agaaagctgg gtgtgacaat atggaggccc aatcgat                           37

<210> SEQ ID NO 13
<211> LENGTH: 18
<212> TYPE: DNA
<213> ORGANISM: Carica papaya

<400> SEQUENCE: 13
atggcaacag ctatagat                                                18

<210> SEQ ID NO 14
<211> LENGTH: 24
<212> TYPE: DNA
<213> ORGANISM: Carica papaya

<400> SEQUENCE: 14
ttaatattcg gatagtttcc ttat                                         24

<210> SEQ ID NO 15
<211> LENGTH: 35
<212> TYPE: DNA
<213> ORGANISM: Carica papaya

<400> SEQUENCE: 15
aaaaagcagg cttcaccatg gcaacagcta tagat                             35

<210> SEQ ID NO 16
<211> LENGTH: 37
<212> TYPE: DNA
<213> ORGANISM: Carica papaya

```
<400> SEQUENCE: 16
agaaagctgg gtgatattcg gatagtttcc ttatagc                              37

<210> SEQ ID NO 17
<211> LENGTH: 24
<212> TYPE: DNA
<213> ORGANISM: Carica papaya

<400> SEQUENCE: 17
atggaaggag agtgttgttc gacg                                            24

<210> SEQ ID NO 18
<211> LENGTH: 24
<212> TYPE: DNA
<213> ORGANISM: Carica papaya

<400> SEQUENCE: 18
tcagtcttca tcggaagttt ccgg                                            24

<210> SEQ ID NO 19
<211> LENGTH: 35
<212> TYPE: DNA
<213> ORGANISM: Carica papaya

<400> SEQUENCE: 19
aaaaagcagg cttcaccatg gaaggagagt gttcg                                35

<210> SEQ ID NO 20
<211> LENGTH: 31
<212> TYPE: DNA
<213> ORGANISM: Carica papaya

<400> SEQUENCE: 20
agaaagctgg gtcttcatcg gaagtttccg g                                    31

<210> SEQ ID NO 21
<211> LENGTH: 18
<212> TYPE: DNA
<213> ORGANISM: Carica papaya

<400> SEQUENCE: 21
atggagggtg gagcggag                                                   18

<210> SEQ ID NO 22
<211> LENGTH: 23
<212> TYPE: DNA
<213> ORGANISM: Carica papaya

<400> SEQUENCE: 22
tcactcgcca tccgaactat ctg                                             23

<210> SEQ ID NO 23
<211> LENGTH: 35
<212> TYPE: DNA
<213> ORGANISM: Carica papaya

<400> SEQUENCE: 23
aaaaagcagg cttcaccatg gagggtggag cggag                                35

<210> SEQ ID NO 24
<211> LENGTH: 37
<212> TYPE: DNA
<213> ORGANISM: Carica papaya
```

```
<400> SEQUENCE: 24
agaaagctgg gtgctcgcca tccgaactat ctgggtc                                    37
```